(12) United States Patent
Mollere

(10) Patent No.: US 8,206,314 B2
(45) Date of Patent: Jun. 26, 2012

(54) MRI BIOPSY TARGETING GRID WITH ROUND OPENINGS

(75) Inventor: Rebecca J. Mollere, Loveland, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 397 days.

(21) Appl. No.: 12/486,229

(22) Filed: Jun. 17, 2009

(65) Prior Publication Data

US 2010/0324448 A1  Dec. 23, 2010

(51) Int. Cl.
*A61B 10/00* (2006.01)
*A61B 19/00* (2006.01)
*A61B 5/05* (2006.01)

(52) U.S. Cl. ......... 600/562; 600/417; 600/564; 606/130
(58) Field of Classification Search .................. 600/417, 600/562–568; 606/130
See application file for complete search history.

(56) References Cited

U.S. PATENT DOCUMENTS

| | | | |
|---|---|---|---|
| 5,056,523 A | 10/1991 | Hotchkiss, Jr. et al. | |
| 5,217,441 A | 6/1993 | Shichman | |
| 5,526,822 A | 6/1996 | Burbank et al. | |
| 5,534,778 A | 7/1996 | Loos et al. | |
| 5,637,074 A | 6/1997 | Andino et al. | |
| 5,649,547 A | 7/1997 | Ritchart et al. | |
| 5,713,869 A | 2/1998 | Morejon | |
| 5,752,768 A | 5/1998 | Assh | |
| 5,769,086 A | 6/1998 | Ritchart et al. | |
| 5,775,333 A | 7/1998 | Burbank et al. | |
| 5,855,554 A | 1/1999 | Schneider et al. | |
| 5,928,164 A | 7/1999 | Burbank et al. | |
| 5,964,716 A | 10/1999 | Gregoire et al. | |
| 5,980,469 A | 11/1999 | Burbank et al. | |
| 6,007,497 A | 12/1999 | Huitema | |
| 6,017,316 A | 1/2000 | Ritchart et al. | |
| 6,077,230 A | 6/2000 | Gregoire et al. | |
| 6,086,544 A | 7/2000 | Hibner et al. | |
| 6,120,462 A | 9/2000 | Hibner et al. | |

(Continued)

FOREIGN PATENT DOCUMENTS

EP   0 640 842   3/1995

(Continued)

OTHER PUBLICATIONS

U.S. Appl. No. 12/337,814, filed Dec. 18, 2008, Parihar et al.

(Continued)

*Primary Examiner* — Max Hindenburg
*Assistant Examiner* — Megan Leedy
(74) *Attorney, Agent, or Firm* — Frost Brown Todd LLC

(57) ABSTRACT

A biopsy system comprises a biopsy device and a localization grid plate, which is configured to localize part of a patient and defines a plurality of round openings. A probe of the biopsy device and/or other associated other components may be inserted through a selected one of the openings. The grid plate may thus guide the probe and/or other components as such components are inserted into the localized part of the patient; and may further support the probe and/or other components after insertion. The grid plate may thus be used without a targeting cube or other inserted guide. Alternatively, the openings of the grid plate may be configured to receive a targeting guide having a cylindraceous body. The guide body may define passageways for inserting a probe or other components, and may be rotatable to position the passageways to selectively define an insertion axis for the probe.

20 Claims, 13 Drawing Sheets

U.S. PATENT DOCUMENTS

| | | | |
|---|---|---|---|
| 6,228,055 B1 | 5/2001 | Foerster et al. | |
| 6,231,522 B1 | 5/2001 | Voegele et al. | |
| 6,273,862 B1 | 8/2001 | Privitera et al. | |
| 6,626,849 B2 | 9/2003 | Huitema et al. | |
| 6,743,177 B2 | 6/2004 | Ito | |
| 6,752,768 B2 | 6/2004 | Burdorff et al. | |
| 7,244,234 B2 | 7/2007 | Ridley et al. | |
| 7,379,769 B2 | 5/2008 | Piron et al. | |
| 7,442,171 B2 | 10/2008 | Stephens et al. | |
| 7,507,210 B2 | 3/2009 | Hibner et al. | |
| 2003/0199753 A1 | 10/2003 | Hibner et al. | |
| 2004/0064149 A1 | 4/2004 | Doern et al. | |
| 2005/0080333 A1* | 4/2005 | Piron et al. | 600/417 |
| 2005/0283069 A1 | 12/2005 | Hughes et al. | |
| 2007/0135821 A1 | 6/2007 | Shabaz | |
| 2007/0167736 A1 | 7/2007 | Dietz et al. | |
| 2007/0233157 A1 | 10/2007 | Mark et al. | |
| 2007/0255168 A1 | 11/2007 | Hibner et al. | |
| 2008/0200836 A1 | 8/2008 | Speeg et al. | |
| 2008/0214955 A1 | 9/2008 | Speeg et al. | |
| 2008/0228103 A1 | 9/2008 | Ritchie et al. | |

FOREIGN PATENT DOCUMENTS

| | | |
|---|---|---|
| EP | 1 815 815 | 8/2007 |
| WO | WO 02/13709 | 2/2002 |
| WO | WO 2007/070285 | 6/2007 |

OTHER PUBLICATIONS

U.S. Appl. No. 12/337,674, filed Dec. 18, 2008, Parihar et al.
U.S. Appl. No. 12/337,874, filed Dec. 18, 2008, Parihar et al.
U.S. Appl. No. 12/337,911, filed Dec. 18, 2008, Parihar et al.
U.S. Appl. No. 12/337,942, filed Dec. 18, 2008, Parihar et al.
EPO Search Report dated Aug. 8, 2007 for Application No. 07251810.3.
EPO Search Report dated Aug. 28, 2007 for Application No. 07251817.8.

* cited by examiner

MRI BIOPSY TARGETING GRID WITH ROUND OPENINGS

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. Merely exemplary biopsy devices are disclosed in U.S. Pat. No. 6,273,862, entitled "Surgical Device for the Collection of Soft Tissue," issued Aug. 14, 2001; U.S. Pat. No. 6,231,522, entitled "Biopsy Instrument with Breakable Sample Segments," issued May 15, 2001; U.S. Pat. No. 6,228,055, entitled "Devices for Marking and Defining Particular Locations in Body Tissue," issued May 8, 2001; U.S. Pat. No. 6,120,462, entitled "Control Method for an Automated Surgical Biopsy Device," issued Sep. 19, 2000; U.S. Pat. No. 6,086,544, entitled "Control Apparatus for an Automated Surgical Biopsy Device," issued Jul. 11, 2000; U.S. Pat. No. 6,077,230, entitled "Biopsy Instrument with Removable Extractor," issued Jun. 20, 2000; U.S. Pat. No. 6,017,316, entitled "Vacuum Control System and Method for Automated Biopsy Device," issued Jan. 25, 2000; U.S. Pat. No. 6,007,497, entitled "Surgical Biopsy Device," issued Dec. 28, 1999; U.S. Pat. No. 5,980,469, entitled "Method and Apparatus for Automated Biopsy and Collection of Soft Tissue," issued Nov. 9, 1999; U.S. Pat. No. 5,964,716, entitled "Method of Use for a Multi-Port Biopsy Instrument," issued Oct. 12, 1999; U.S. Pat. No. 5,928,164, entitled "Apparatus for Automated Biopsy and Collection of Soft Tissue," issued Jul. 27, 1999; U.S. Pat. No. 5,775,333, entitled "Apparatus for Automated Biopsy and Collection of Soft Tissue," issued Jul. 7, 1998; U.S. Pat. No. 5,769,086, entitled "Control System and Method for Automated Biopsy Device," issued Jun. 23, 1998; U.S. Pat. No. 5,649,547, entitled "Methods and Devices for Automated Biopsy and Collection of Soft Tissue," issued Jul. 22, 1997; U.S. Pat. No. 5,526,822, entitled "Method and Apparatus for Automated Biopsy and Collection of Soft Tissue," issued Jun. 18, 1996; U.S. Pub. No. 2008/0214955, entitled "Presentation of Biopsy Sample by Biopsy Device," published Sep. 4, 2008; U.S. Pub. No. 2007/0255168, entitled "Grid and Rotatable Cube Guide Localization Fixture for Biopsy Device," published Nov. 1, 2007; U.S. Pub. No. 2007/0118048, entitled "Remote Thumbwheel for a Surgical Biopsy Device," published May 24, 2007; U.S. Pub. No. 2005/0283069, entitled "MRI Biopsy Device Localization Fixture," published Dec. 22, 2005; U.S. Pub. No. 2003/0199753, entitled "MRI Compatible Biopsy Device with Detachable Probe," published Oct. 23, 2003; U.S. Pub. No. 2003/0109803, entitled "MRI Compatible Surgical Biopsy Device," published Jun. 12, 2003; U.S. Provisional Patent Application Ser. No. 60/874,792, entitled "Biopsy Sample Storage," filed Dec. 13, 2006; and U.S. Provisional Patent Application Ser. No. 60/869,736, entitled "Biopsy System," filed Dec. 13, 2006. The disclosure of each of the above-cited U.S. patents, U.S. patent application Publications, and U.S. Provisional patent applications is incorporated by reference herein.

Some biopsy systems may provide an apparatus to guide a probe and/or other components of a biopsy device to a desired biopsy site. In some such biopsy systems, a guide cube and positioning grid plate may be used. The guide cube may be selectively located within an opening in the grid plate. The guide cube may include guide holes to receive a portion of the probe and/or other components, for example a needle, cannula, obturator, or combinations of these or other components. With the guide cube inserted in the grid plate, the probe or other components can be guided through a selected guide hole of the guide cube to arrive at a desired biopsy site. The desired biopsy site may or may not have been identified and/or targeted by one or more of the guidance approaches mentioned above.

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

As shown in the figures, an exemplary magnetic resonance imaging (MRI or MR imaging) compatible biopsy system may include a control module (12), localization assembly (15), and biopsy device (14). In particular, localization assembly (15) is configured to localize a patient's breast and guide needle (90) of biopsy device (14) to a targeted area within the patient's breast; while control module (12) is operable to control biopsy device (14) after needle (90) has been introduced to the target site. These components and their sub-components will be discussed further below. In addition, targeting guides for use with various localization assemblies will be discussed. While this disclosure may reference the biopsy system as compatible with MRI and MRI equipment and devices, it should be appreciated that other imaging techniques and equipment and devices may be used with the components described below, including but not limited to stereotactic, ultrasound, PEM, BSGI, and/or other imaging techniques and equipment.

I. Control Module

Figure 1:
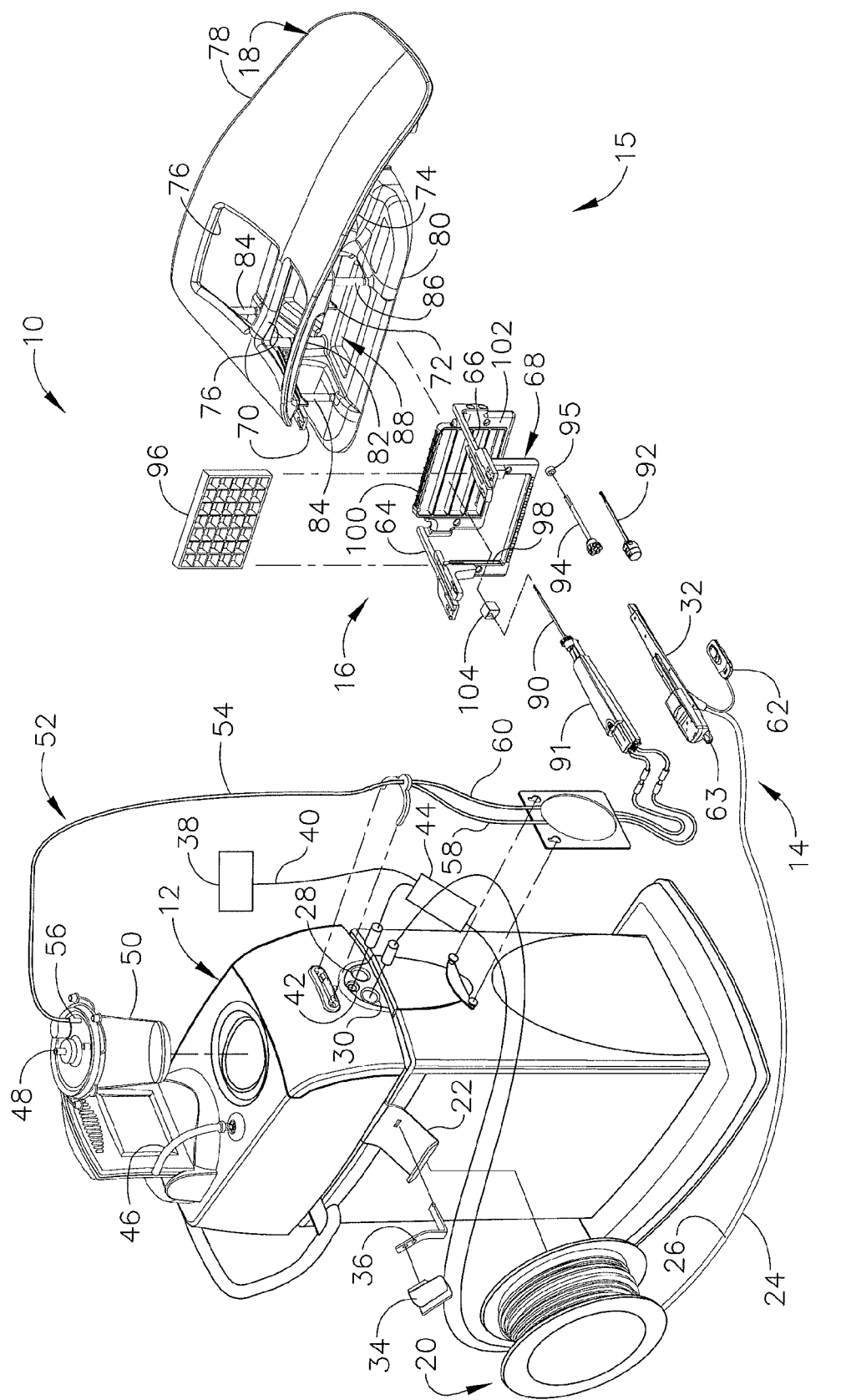
FIG. 1 is a perspective view of a biopsy system including a control module remotely coupled to a biopsy device, and including a localization assembly.
Figure 2:
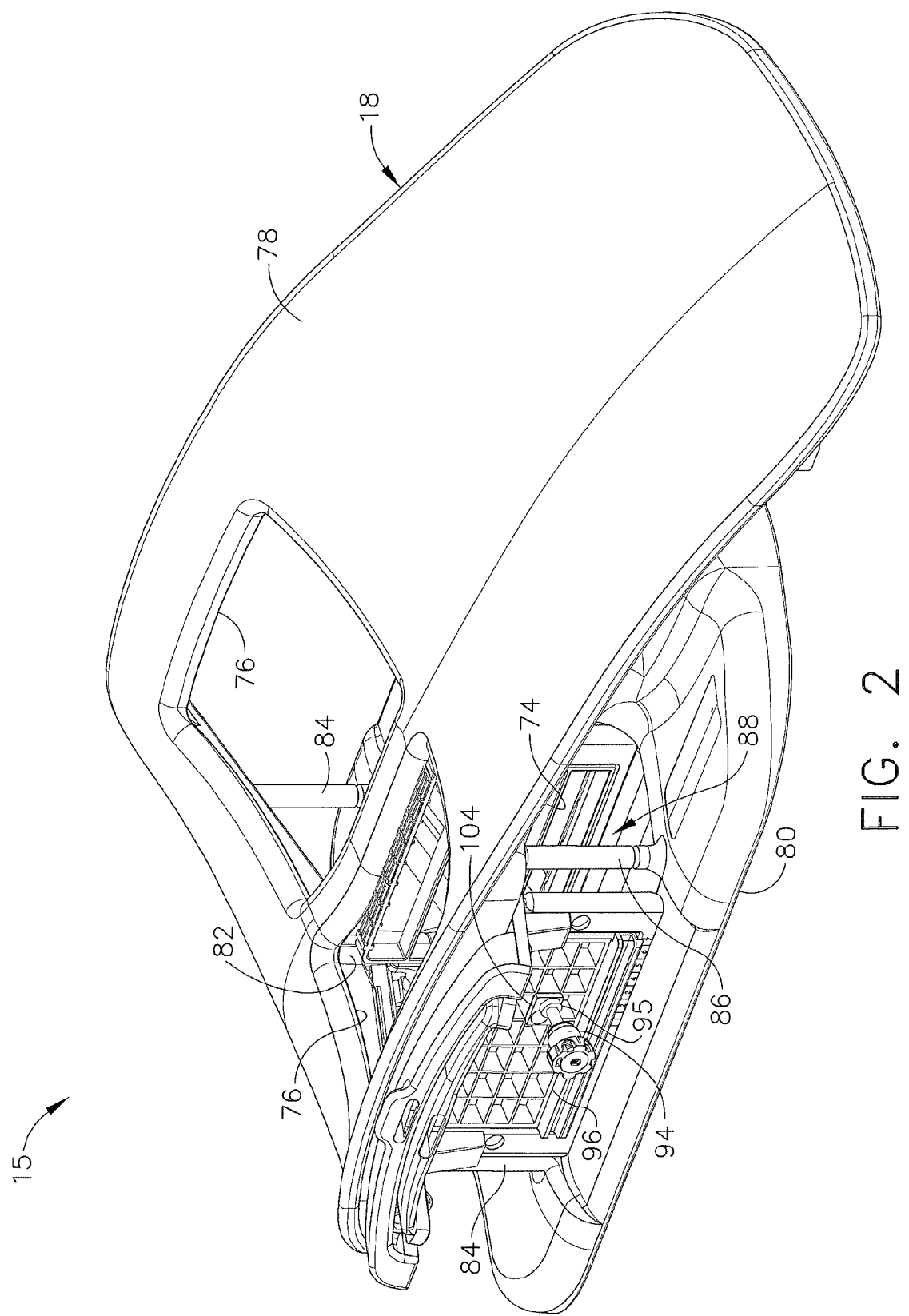
FIG. 2 is a perspective view of a breast coil of the localization assembly of FIG. 1.
Figure 3:
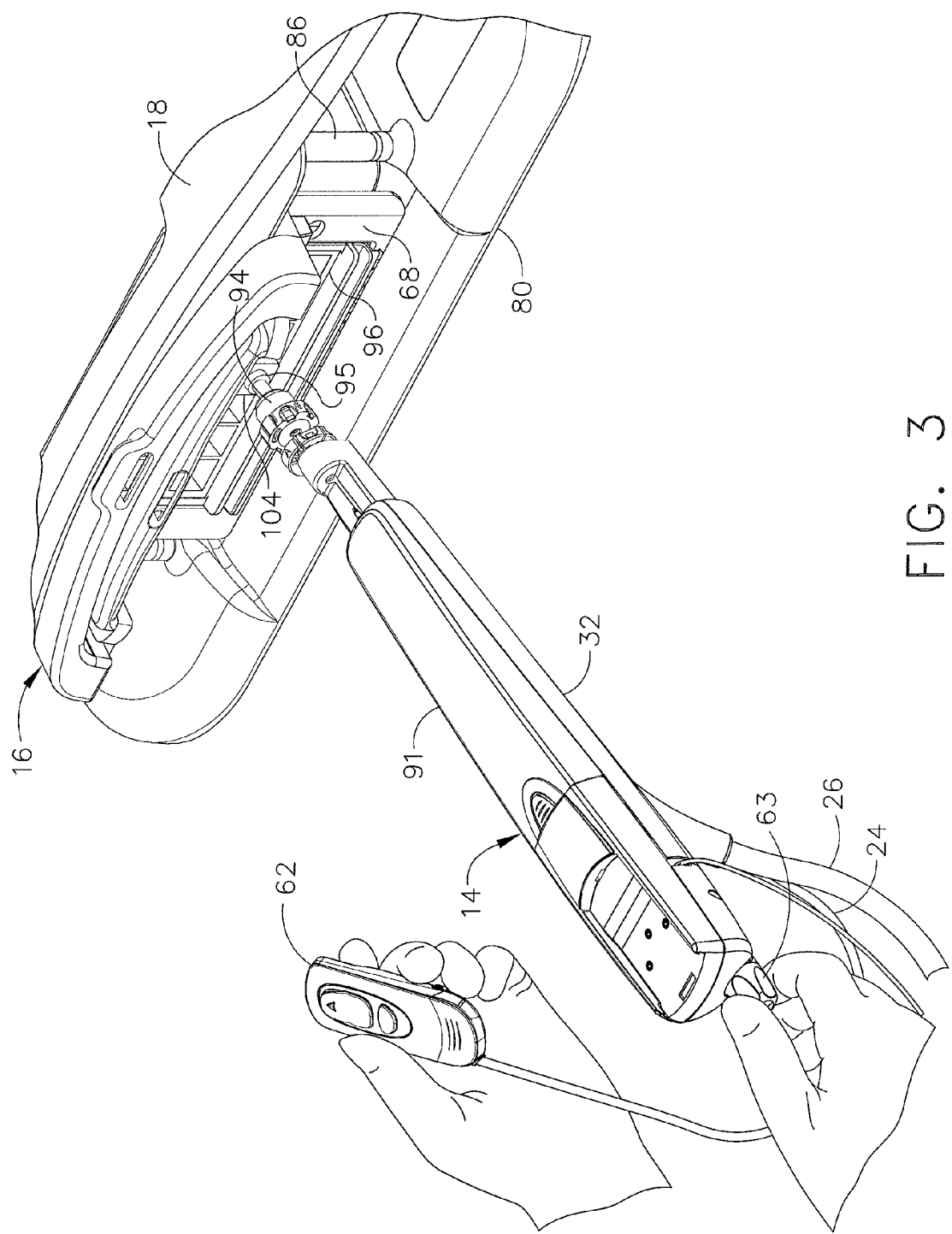
FIG. 3 is a perspective view of the biopsy device inserted through the guide cube of the localization assembly of FIG. 1.

In FIGS. 1-3, MRI compatible biopsy system (10) has control module (12) that may be placed outside of a shielded room containing an MRI machine (not shown) or at least spaced away to mitigate detrimental interaction with its strong magnetic field and/or sensitive radio frequency (RF) signal detection antennas. As described in U.S. Pat. No. 6,752,768, which is hereby incorporated by reference in its entirety, a range of preprogrammed functionality may be incorporated into control module (12) to assist in taking tissue samples. Control module (12) controls and powers biopsy device (14) that is used with localization assembly (15). Biopsy device (14) is positioned and guided by localization fixture (16) attached to breast coil (18) that may be placed upon a gantry (not shown) of a MRI or other imaging machine.

In the present example, control module (12) is mechanically, electrically, and pneumatically coupled to biopsy device (14) so that components may be segregated that need to be spaced away from the strong magnetic field and the sensitive RF receiving components of a MRI machine. Cable management spool (20) is placed upon cable management attachment saddle (22) that projects from a side of control module (12). Wound upon cable management spool (20) is paired electrical cable (24) and mechanical cable (26) for communicating control signals and cutter rotation/advancement motions respectively. In particular, electrical and mechanical cables (24, 26) each have one end connected to respective electrical and mechanical ports (28, 30) in control module (12) and another end connected to holster portion (32) of biopsy device (14). Docking cup (34), which may hold holster portion (32) when not in use, is hooked to control module (12) by docking station mounting bracket (36). It should be understood that such components described above as being associated with control module (12) are merely optional.

Interface lock box (38) mounted to a wall provides tether (40) to lockout port (42) on control module (12). Tether (40) is uniquely terminated and of short length to preclude inadvertent positioning of control module (12) too close to a MRI machine or other machine. In-line enclosure (44) may register tether (40), electrical cable (24) and mechanical cable (26) to their respective ports (42, 28, 30) on control module (12).

Vacuum assist is provided by first vacuum line (46) that connects between control module (12) and outlet port (48) of vacuum canister (50) that catches liquid and solid debris. Tubing kit (52) completes the pneumatic communication between control module (12) and biopsy device (14). In particular, second vacuum line (54) is connected to inlet port (56) of vacuum canister (50). Second vacuum line (54) divides into two vacuum lines (58, 60) that are attached to biopsy device (14). With biopsy device (14) installed in holster portion (32), control module (12) performs a functional check. Saline may be manually injected into biopsy device (14) or otherwise introduced to biopsy device (14), such as to serve as a lubricant and to assist in achieving a vacuum seal and/or for other purposes. Control module (12) actuates a cutter mechanism (not shown) in biopsy device (14), monitoring full travel of a cutter in biopsy device (14) in the present example. Binding in mechanical cable (26) or within biopsy device (14) may be optionally monitored with reference to motor force exerted to turn mechanical cable (26) and/or an amount of twist in mechanical cable (26) may be sensed in comparing rotary speed or position at each end of mechanical cable (26).

Remote keypad (62), which is detachable from holster portion (32), communicates via electrical cable (24) to control panel (12) to enhance clinician control of biopsy device (14) in the present example, especially when controls that would otherwise be on biopsy device (14) itself are not readily accessible after insertion into localization fixture (16) and/or placement of control module (12) is inconveniently remote (e.g., 30 feet away). However, as with other components described herein, remote keypad (62) is merely optional, and may be modified, substituted, supplemented, or omitted as desired. In the present example, aft end thumbwheel (63) on holster portion (32) is also readily accessible after insertion to rotate the side from which a tissue sample is to be taken.

Of course, the above-described control module (12) is merely one example. Any other suitable type of control module (12) and associated components may be used. By way of example only, control module (12) may instead be configured and operable in accordance with the teachings of U.S. Pub. No. 2008/0228103, entitled "Vacuum Timing Algorithm for Biopsy Device," published Sep. 18, 2008, the disclosure of which is incorporated by reference herein. As another merely illustrative example, control module (12) may instead be configured and operable in accordance with the teachings of U.S. patent application Ser. No. 12/337,814, entitled "Control Module Interface for MRI Biopsy Device," filed Dec. 18, 2008, the disclosure of which is incorporated by reference herein. Alternatively, control module (12) may have any other suitable components, features, configurations, functionalities, operability, etc. Other suitable variations of control module (12) and associated components will be apparent to those of ordinary skill in the art in view of the teachings herein.

II. Localization Assembly

Localization assembly (15) of the present example comprises breast coil (18) and localization fixture (16). These components of localization assembly (15) are described further below.

Left and right parallel upper guides (64, 66) of localization framework (68) are laterally adjustably received respectively within left and right parallel upper tracks (70, 72) attached to under side (74) and to each side of a selected breast aperture (76) formed in patient support platform (78) of breast coil (18). Base (80) of breast coil (18) is connected by centerline pillars (82) that are attached to patient support platform (78) between breast apertures (76). Also, a pair of outer vertical support pillars (84, 86) on each side spaced about a respective breast aperture (76) respectively define lateral recess (88) within which localization fixture (16) resides.

It should be appreciated that the patient's breasts hang pendulously respectively into breast apertures (76) within lateral recesses (88) in the present example. For convenience, herein a convention is used for locating a suspicious lesion by Cartesian coordinates within breast tissue referenced to localization fixture (16) and to thereafter selectively position an instrument, such as needle (90) of probe (91) that is engaged to holster portion (32) to form biopsy device (14). Of course, any other type of coordinate system or targeting techniques may be used. To enhance hands-off use of biopsy system (10), especially for repeated re-imaging within the narrow confines of a closed bore MRI machine, biopsy system (10) may also guide obturator (92) encompassed by cannula (94). Depth of insertion is controlled by depth stop device (95) longitudinally positioned on either needle (90) or cannula (94). Alternatively, depth of insertion may be controlled in any other suitable fashion.

This guidance is specifically provided by a lateral fence in the present example, depicted as a grid plate (96), which is received within laterally adjustable outer three-sided plate bracket (98) attached below left and right parallel upper guides (64, 66). Similarly, a medial fence with respect to a medial plane of the chest of the patient, depicted as medial plate (100), is received within inner three-sided plate bracket (102) attached below left and right parallel upper guides (64, 66) close to centerline pillars (82) when installed in breast coil (18). To further refine the insertion point of the instrument (e.g., needle (90) of probe (91), obturator/cannula (92, 94), etc.), guide cube (104) may be inserted into grid plate (96).

In the present example, the selected breast is compressed along an inner (medial) side by medial plate (100) and on an outer (lateral) side of the breast by grid plate (96), the latter defining an X-Y plane. The X-axis is vertical (sagittal) with respect to a standing patient and corresponds to a left-to-right axis as viewed by a clinician facing the externally exposed portion of localization fixture (16). Perpendicular to this X-Y plane extending toward the medial side of the breast is the Z-axis, which typically corresponds to the orientation and depth of insertion of needle (90) or obturator/cannula (92, 94) of biopsy device (14). For clarity, the term Z-axis may be used interchangeably with "axis of penetration", although the latter may or may not be orthogonal to the spatial coordinates used to locate an insertion point on the patient. Versions of localization fixture (16) described herein allow a non-orthogonal axis of penetration to the X-Y axis to a lesion at a convenient or clinically beneficial angle.

It should be understood that the above-described localization assembly (15) is merely one example. Any other suitable type of localization assembly (15) may be used, including but not limited to localization assemblies (15) that use a breast coil (18) and/or localization fixture (16) different from those described above. Other suitable components, features, configurations, functionalities, operability, etc. for a localization assembly (15) will be apparent to those of ordinary skill in the art in view of the teachings herein.

III. Biopsy Device

As shown in FIG. 1, one version of biopsy device (14) may comprise holster portion (32) and probe (91). Exemplary holster portion (32) was discussed previously in the above section addressing control module (12). The following paragraphs will discuss probe (91) and associated components and devices in further detail.

Figure 4:
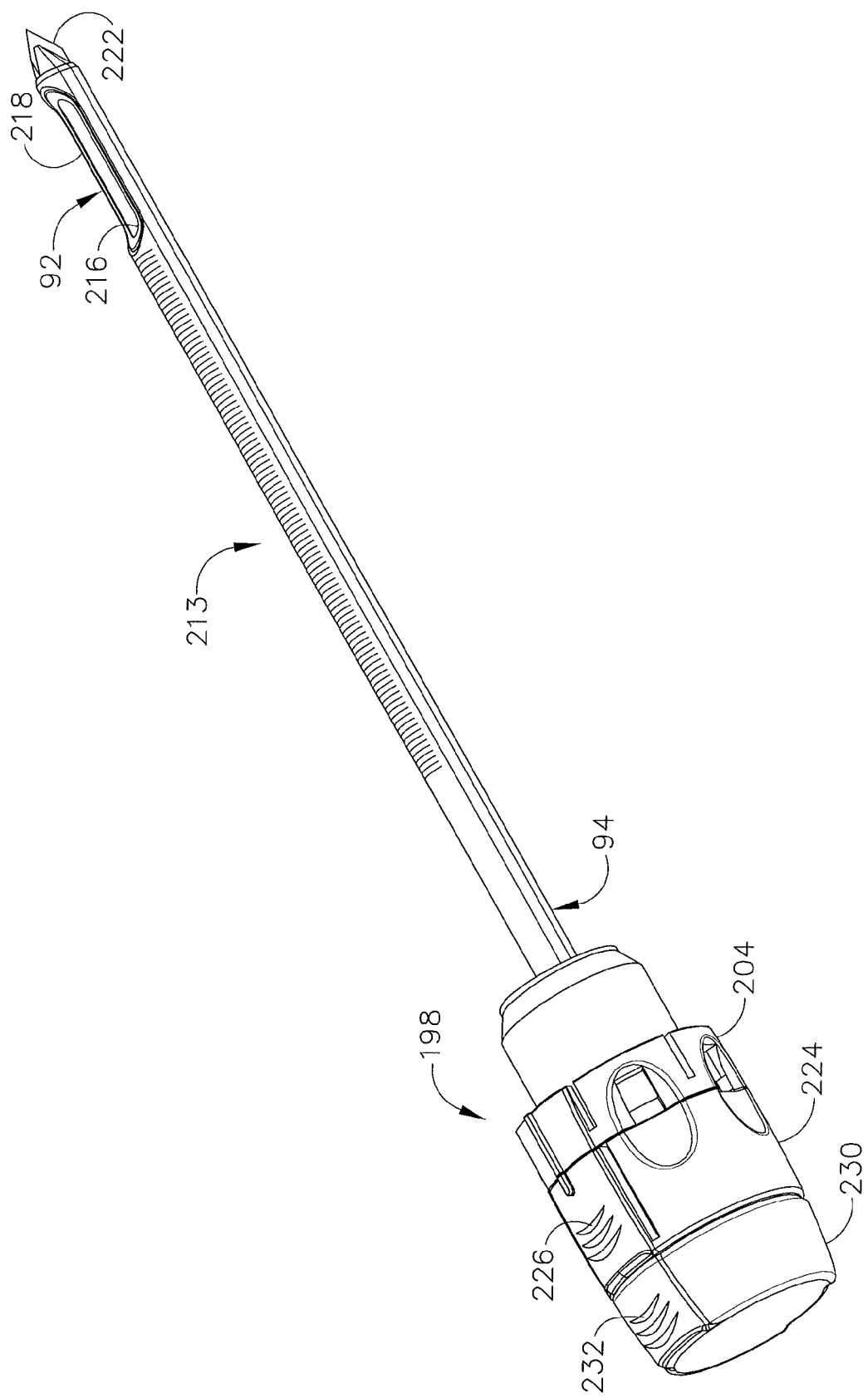
FIG. 4 is a perspective view of the obturator and cannula of the biopsy system of FIG. 1.
Figure 5:
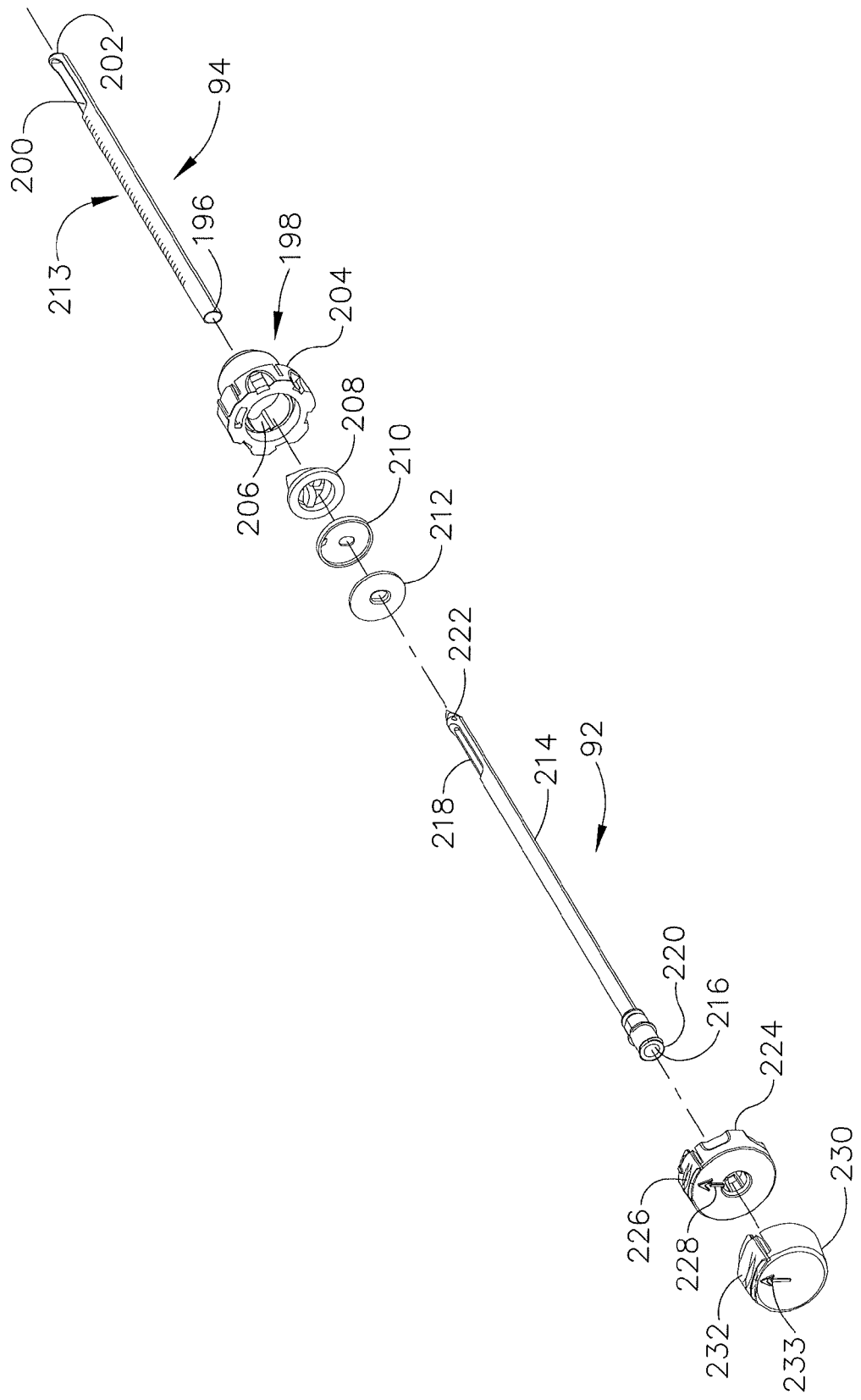
FIG. 5 is an exploded perspective view of the obturator and cannula of FIG. 4.
Figure 6:
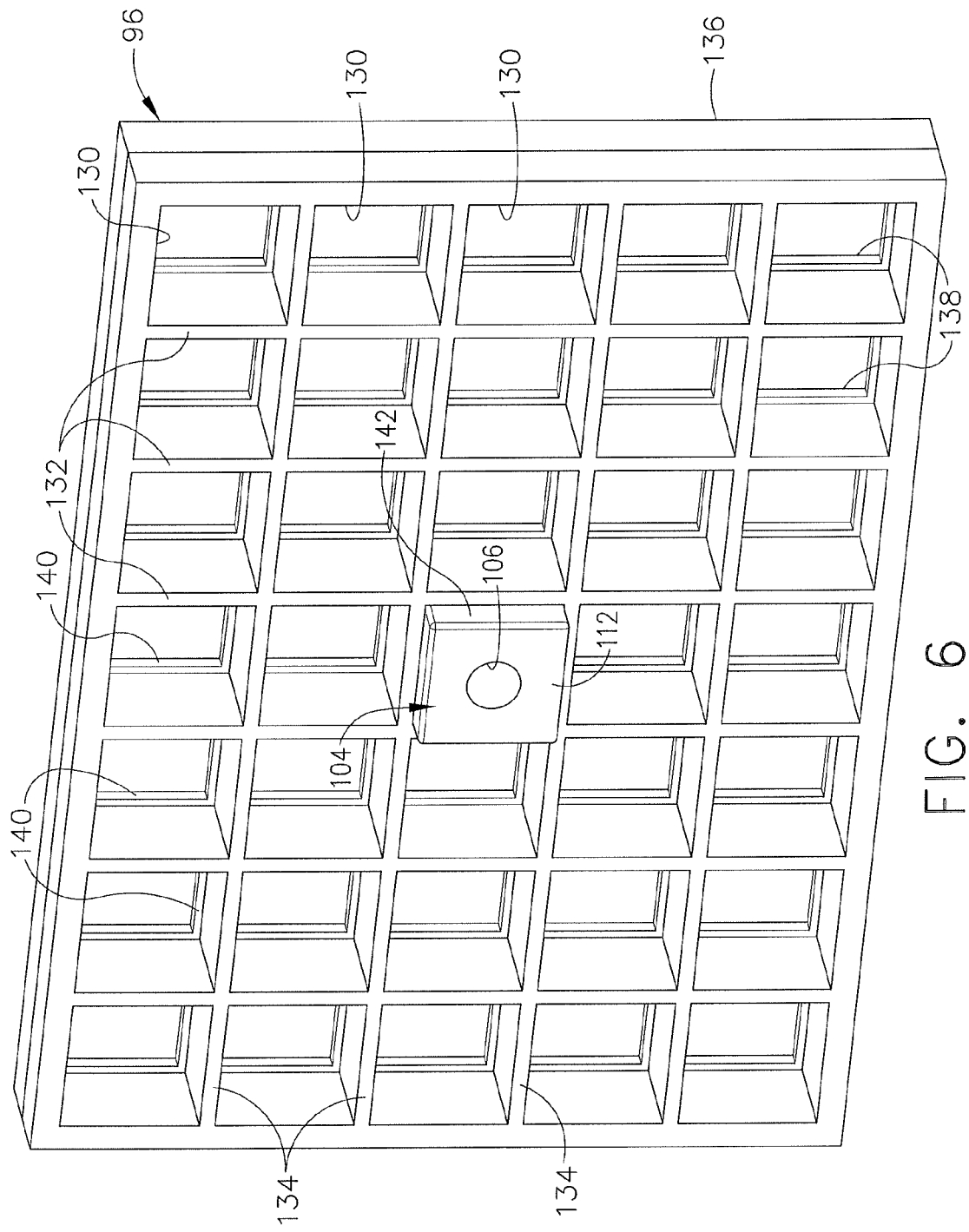
FIG. 6 is a perspective view of the guide cube inserted into the grid plate of the localization assembly of FIG. 1.
Figure 7:
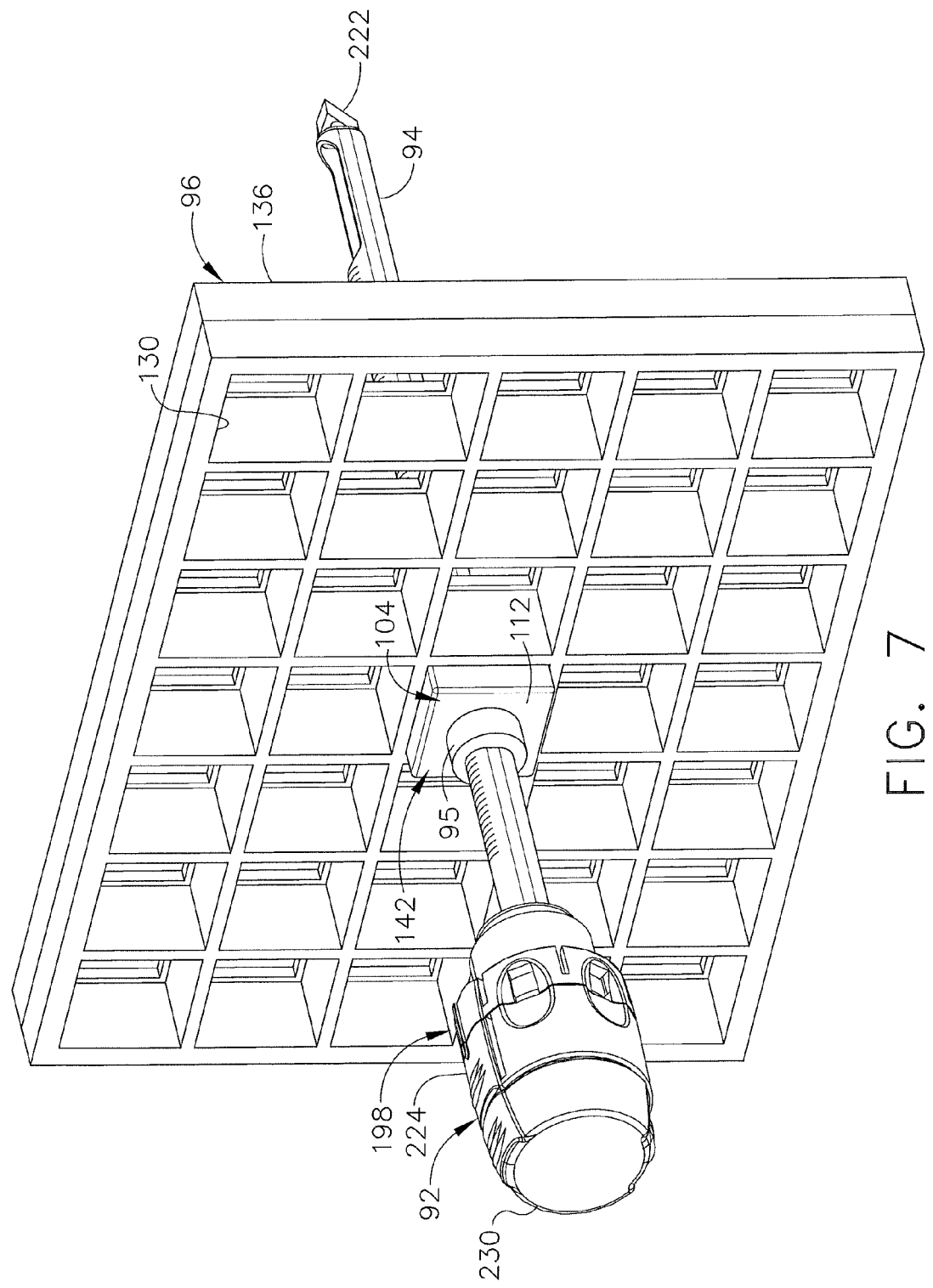
FIG. 7 is a perspective view of the obturator and cannula of FIG. 4 with a depth stop device of FIG. 1 inserted through the guide cube and grid plate of FIG. 6.

In the present example, cannula (94) and obturator (92) are associated with probe (91). In particular, and as shown in FIGS. 4, 5, and 7, obturator (92) is slid into cannula (94) and the combination is guided through guide cube (104) to the biopsy site within the breast tissue. Obturator (92) is then withdrawn from cannula (94), then needle (90) of probe (91) is inserted in cannula (94), and then biopsy device (14) is operated to acquire one or more tissue samples from the breast via needle (90).

Cannula (94) of the present example is proximally attached to cylindrical hub (198) and cannula (94) includes lumen (196) and lateral aperture (200) proximate to open distal end (202). Cylindrical hub (198) has exteriorly presented thumbwheel (204) for rotating lateral aperture (200). Cylindrical hub (198) has interior recess (206) that encompasses duckbill seal (208), wiper seal (210) and seal retainer (212) to provide a fluid seal when lumen (196) is empty and for sealing to inserted obturator (92). Longitudinally spaced measurement indicia (213) along an outer surface of cannula (94) visually, and perhaps physically, provide a means to locate depth stop device (95) of FIG. 1.

Obturator (92) of the present example incorporates a number of components with corresponding features. Hollow shaft (214) includes fluid lumen (216) that communicates between imageable side notch (218) and proximal port (220). Hollow shaft (214) is longitudinally sized to extend, when fully engaged with cannula (94), piercing tip (222) out of distal end (202) of cannula (94). Obturator thumbwheel cap (224) encompasses proximal port (220) and includes locking feature (226), which includes visible angle indicator (228), and which engages cannula thumbwheel (204) to ensure that imageable side notch (218) is registered to lateral aperture (200) in cannula (94). Obturator seal cap (230) may be engaged proximally into obturator thumbwheel cap (224) to close fluid lumen (216). Obturator seal cap (230) of the present example includes locking or locating feature (232) that includes visible angle indicator (233) that corresponds with visible angle indicator (228) on obturator thumbwheel cap (224), which may be fashioned from either a rigid, soft, or elastomeric material. In FIG. 7, guide cube (104) has guided obturator (92) and cannula (94) through grid plate (96).

While obturator (92) of the present example is hollow, it should be understood that obturator (92) may alternatively have a substantially solid interior, such that obturator (92) does not define an interior lumen. In addition, obturator (92) may lack side notch (218) in some versions. Other suitable components, features, configurations, functionalities, operability, etc. for an obturator (92) will be apparent to those of ordinary skill in the art in view of the teachings herein. Likewise, cannula (94) may be varied in a number of ways. For instance, in some other versions, cannula (94) has a closed distal end (202). As another merely illustrative example, cannula (94) may have a closed piercing tip (222) instead of obturator (92) having piercing tip (222). In some such versions, obturator (92) may simply have a blunt distal end; or the distal end of obturator (92) may have any other suitable structures, features, or configurations. Other suitable components, features, configurations, functionalities, operability, etc. for a cannula (94) will be apparent to those of ordinary skill in the art in view of the teachings herein. Furthermore, in some versions, one or both of obturator (92) or cannula (94) may be omitted altogether. For instance, needle (90) of probe (91) may be directly inserted into a guide cube (104), without being inserted into guide cube (104) via cannula (94). It should be noted that, while the term "cannula" is used to refer to cannula (94), which is configured to receive obturator (92), needle (90) of probe (91) may also be regarded as a "cannula," even though needle (90) of the present example does not receive obturator (92).

Another component that may be used with probe (91) (or needle (90)) is depth stop (95). Depth stop may be of any suitable configuration that is operable to prevent cannula (94) and obturator (92) (or needle (90)) from being inserted further than desired. For instance, depth stop (95) may be positioned on the exterior of cannula (94) (or needle (90)), and may be configured to restrict the extent to which cannula (94) is inserted into a guide cube. It should be understood that such restriction by depth stop (95) may further provide a limit on the depth to which the combination of cannula (94) and obturator (92) (or needle (90)) may be inserted into the patient's breast. Furthermore, it should be understood that such restriction may establish the depth within the patient's breast at which biopsy device (14) acquires one or more tissue samples after obturator (92) has been withdrawn from cannula (94) and needle (90) has been inserted in cannula (94). Exemplary depth stops (95) that may be used with biopsy system (10) are described in U.S. Pub. No. 2007/0255168, entitled "Grid and Rotatable Cube Guide Localization Fixture for Biopsy Device," published Nov. 1, 2007, and incorporated by reference herein as mentioned previously.

In the present example, and as noted above, biopsy device (14) includes a needle (90) that may be inserted into cannula (94) after the combination of cannula (94) and obturator (92) has been inserted to a desired location within a patient's breast and after obturator (92) has been removed from cannula (94). Needle (90) of the present example comprises a lateral aperture (not shown) that is configured to substantially align with lateral aperture (200) of cannula (94) when needle (90) is inserted into lumen (196) of cannula (94). Probe (91) of the present example further comprises a rotating and translating cutter (not shown), which is driven by components in holster (32), and which is operable to sever tissue protruding through lateral aperture (200) of cannula (94) and the lateral aperture of needle (90). Severed tissue samples may be retrieved from biopsy device (14) in any suitable fashion.

Figure 8:
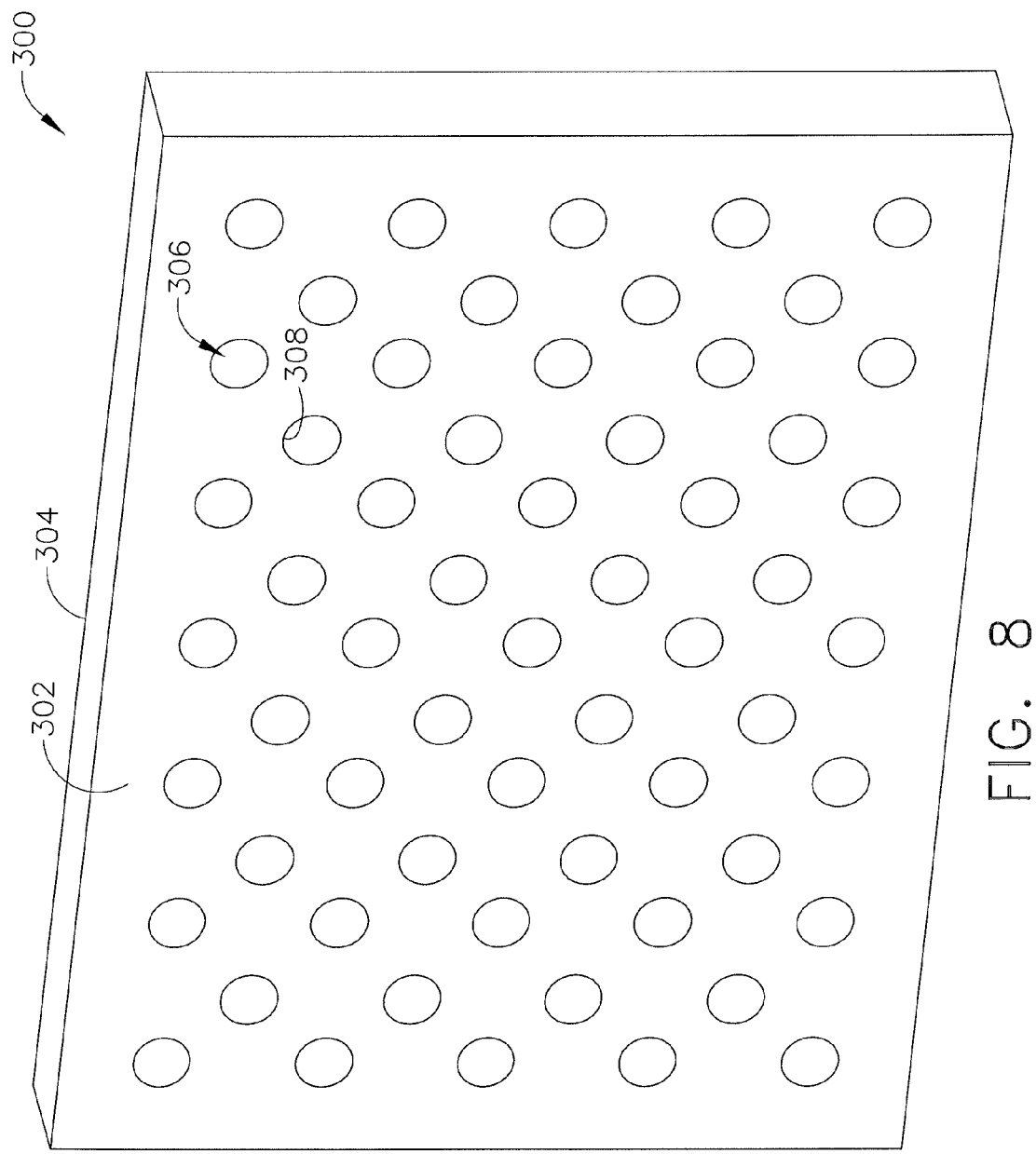
FIG. 8 is a perspective view of an exemplary alternative grid plate.
Figure 9:
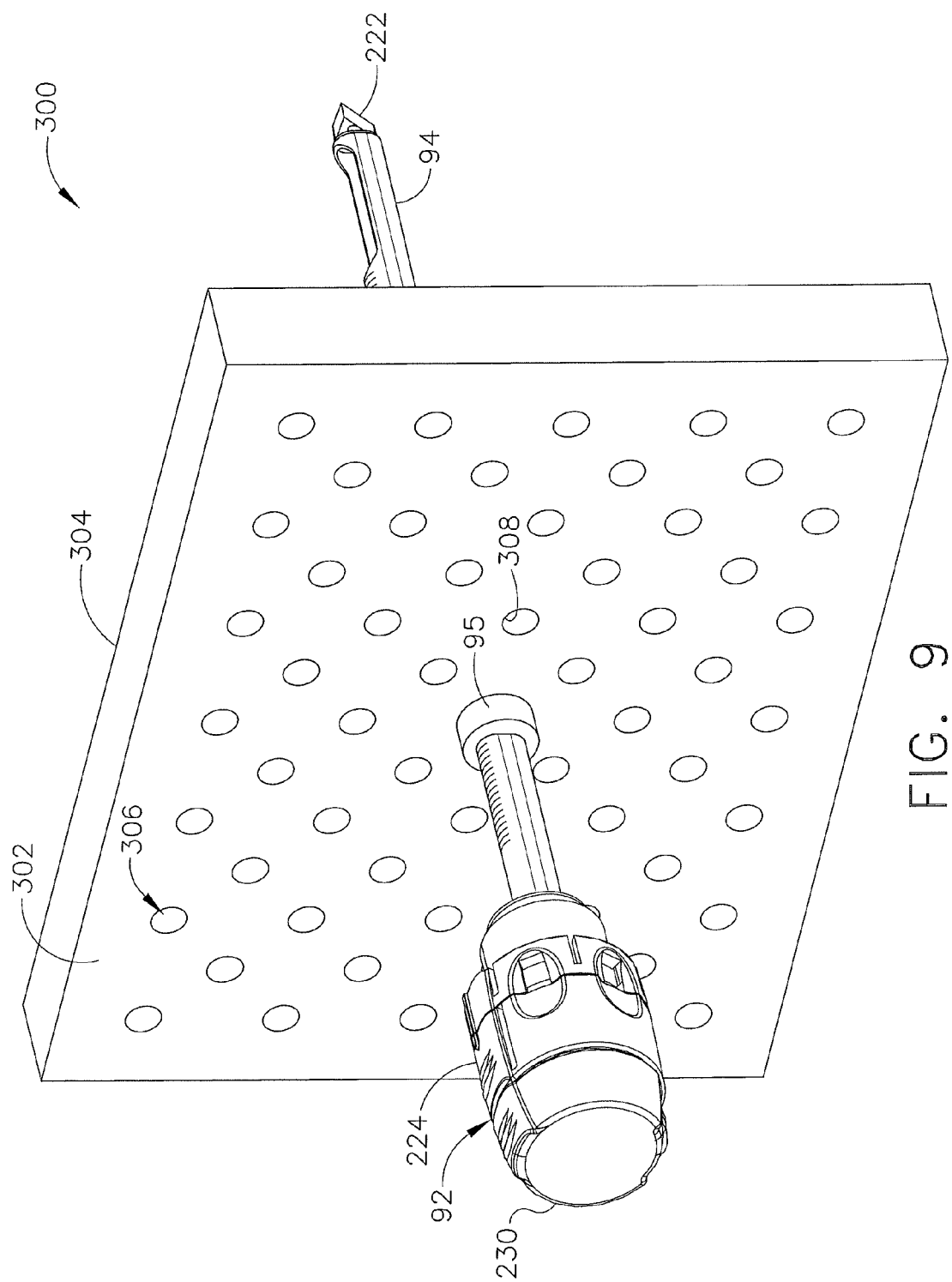
FIG. 9 is a perspective view of the obturator and cannula of FIG. 4 with a depth stop device of FIG. 1 inserted through the guide cube and grid plate of FIG. 8.

By way of example only, biopsy device (14) may be configured and operable in accordance with the teachings of U.S. Pub. No. 2008/0228103, entitled "Vacuum Timing Algorithm for Biopsy Device," published Sep. 18, 2008, the disclosure of which is incorporated by reference herein. As another merely illustrative example, biopsy device (14) may be configured and operable in accordance with the teachings of U.S. patent application Ser. No. 12/337,874, entitled "Mechanical Tissue Sample Holder Indexing Device," filed Dec. 18, 2008, the disclosure of which is incorporated by reference herein. As another merely illustrative example, biopsy device (14) may be configured and operable in accordance with the teachings of U.S. patent application Ser. No. 12/337,674, entitled "Biopsy Device with Sliding Cutter Cover," filed Dec. 18, 2008, the disclosure of which is incorporated by reference herein. By way of example only, cannula (94) may be replaced with any of the detachable needles described in U.S. patent application Ser. No. 12/337,674, entitled "Biopsy Device with Sliding Cutter Cover." As another merely illustrative example, biopsy device (14) may be configured and operable in accordance with the teachings of U.S. patent application Ser. No. 12/337,911, entitled "Biopsy Device with Discrete Tissue Chambers," filed Dec. 18, 2008, the disclosure of which is incorporated by reference herein. As another merely illustrative example, biopsy device (14) may be configured and operable in accordance with the teachings of U.S. patent application Ser. No. 12/337,942, entitled "Biopsy Device with Central Thumbwheel," filed Dec. 18, 2008, the disclosure of which is incorporated by reference herein. As yet another merely illustrative example, biopsy device (14) may be configured and operable in accordance with the teachings of any of the other U.S. patents, U.S. patent application Publications, and U.S. Provisional patent applications that are cited and incorporated by reference herein. Alternatively, biopsy device (14) may have any other suitable components, features, configurations, functionalities, operability, etc. Other suitable variations of biopsy device (14) and associated components will be apparent to those of ordinary skill in the art in view of the teachings herein IV. Alternative Localization Assembly FIGS. 8-9 show an example of alternative grid plate (300) that may be used with localization assembly (15) in lieu of grid plate (96). In particular, grid plate (300) of this example may be received within laterally adjustable outer three-sided plate bracket (98) attached below left and right parallel upper guides (64, 66), similar to grid plate (300) as described above; and may be used to both compress a patient's breast and guide a portion of biopsy device (14) to reach a biopsy target site in the patient's breast. Grid plate (300) comprises a first face (302) and an opposing second face (304). A plurality of guide openings (306) provide passageways from first face (302) to second face (304). Guide openings (306) of the present example are sized to receive a portion of a biopsy device (14). By way of example only, and as shown in FIG. 9, a combination of obturator (92) and cannula (94) may be inserted through a selected one of guide openings (306). Grid plate (300) may thus be used to guide a combination of obturator (92) and cannula (94) (or needle (90)) into a patient's breast without requiring a guide cube (104) or other similar component to be coupled with grid plate (300) at the selected guide opening (306).

In some versions, a combined obturator (92) and cannula (94) are first inserted into a patient's breast via a selected one of guide openings (306). Obturator (92) is then removed from cannula (94), and needle (90) of probe (91) is then inserted into cannula (94) to obtain a tissue sample through side notch (218). In some other versions, obturator (92) and cannula (94) are not used, and needle (90) of probe (91) is inserted directly into a patient's breast via a selected one of guide openings (306). In either case, grid plate (300) may substantially support biopsy device (14) when needle (90) is disposed directly or indirectly in a selected guide opening (306). Alternatively, some other component may directly support the weight of at least a portion of biopsy device (14).

It should be understood that a depth stop (95) may be used as described herein, to restrict the depth to which the combination of obturator (92) and cannula (94) (or needle (90), etc.) may be inserted through a selected guide opening (306); and, hence, restrict the depth to which the combination of obturator (92) and cannula (94) (or needle (90), etc.) may be inserted into a patient's breast. Depth stop (95) may directly abut first face (302) of grid plate (300). Alternatively, a depth stop (95) may be used in any other suitable fashion; or may be modified, substituted, supplemented, or even omitted, as desired.

In the present example, guide openings (306) are spaced substantially equidistantly from each other, and are arranged in a substantially symmetric fashion. It should be understood, however, that guide openings (306) may instead be spaced and/or arranged in any other suitable fashion. For instance, guide openings (306) in one or more sets of guide openings (306) may partially overlap each other, such as the overlapping guide holes shown in FIG. 18 of U.S. Pat. No. 7,507,210, entitled "Biopsy Cannula Adjustable Depth Stop," issued Mar. 24, 2009, the disclosure of which is incorporated by reference herein. Other suitable positions and arrangements of guide openings (306) will be apparent to those of ordinary skill in the art in view of the teachings herein.

It should also be understood that guide openings (306) may have any suitable size. For instance, as noted above, guide openings (306) of the present example are sized to receive a cannula (94) or needle (90). In some settings, a user may have the option to use cannulas (94) and/or needles (90) of various gauges. Accordingly, some versions of grid plate (300) may have guide openings (306) of various sizes that accept cannulas (94) and/or needles (90) of various gauges. Alternatively, the size of guide openings (306) in a given grid plate (300) may be substantially consistent, with different grid plates (300) being available that have openings (306) of different sizes, such that the user may select a particular grid plate (300) based on the gauge of the cannula (94) and/or needle (90) to be used. As yet another merely illustrative example, and as will be described in greater detail below, guide openings (306) may be configured such that each guide opening (306) may accept cannulas (94) and/or needles (90) of different sizes. As still another merely illustrative example, guide openings (306) may be larger, and may be sized to accept a cylindraceous targeting guide (400, 450) as described in greater detail below. Still other suitable sizes for guide openings (306) will be apparent to those of ordinary skill in the art in view of the teachings herein.

Guide openings (306) of the present example are substantially round, and are configured to complement the cross-sectional shape of a cannula (94) or needle that will be inserted into guide openings (306). By way of example only, guide openings (306) may have a substantially circular cross-section, elliptical cross-section, oblong cross-section, "figure eight" type of cross-section, or any other suitable round cross-section. Alternatively, guide openings (306) may have a non-round shape or may have any other suitable configuration.

In the present example, guide plate (300) is formed of a substantially rigid material, such as plastic. Of course, any other suitable material or combination of materials may be used. Also in the present example, the material defining the interior (308) of guide openings (306) is substantially rigid. It should be understood, however, that the material defining the interior (308) of guide openings (306) may have any other suitable properties. For instance, an insert (not shown) may be positioned in each guide opening (306), such that the insert defines the interior (308) of each guide opening (306). By way of example only, such an insert may have elastomeric properties. Suitable elastomeric materials may include thermosetting plastics that may require vulcanization, thermoplastic elastomers (e.g., Santoprene™ among others), natural rubber, synthetic rubbers (e.g. ethylene propylene diene M-class—EPDM—among others), and/or any other suitable materials, including combinations of materials. Providing elastomeric properties or similar properties in guide openings (306) may reduce the likelihood that in instrument (e.g., needle (90) of biopsy device (14), a combination of cannula (94) and obturator (92), etc.) that is inserted through a selected guide opening (306) will inadvertently slip along its longitudinal axis, inadvertently rotate about its longitudinal axis, etc. Providing elastomeric properties or similar properties in guide openings (306) may also permit openings (306) to snugly accept insertion of cannulas (94) and/or needles (90) of different gauges. It should also be understood that when at least a portion of the interior of guide openings (306) is formed of an elastomeric material, guide openings (306) may be formed as longitudinally extending slits through such elastomeric material (e.g., instead of being formed as lumens having circular or otherwise round cross-sections along their length, etc.).

In addition to or in lieu of providing an elastomeric material within guide openings (306), a malleable material or other angulation feature may be provided in or by guide openings (306). For instance, in some settings, it may be desirable to insert a combination of obturator (92) and cannula (94) (or needle (90)) into a patient's breast at a non-orthogonal angle (e.g., non-perpendicular to the plane defined by grid plate (300)). Having malleable material or some other type of angulation feature may permit a user to adjust the angular orientation of a selected guide opening (306) to provide such a non-orthogonal axis of penetration. In some such versions, the malleable material or angulation feature may permit the axis of penetration angle to be adjusted yet still maintain the adjusted axis of penetration angle after insertion of the combination of obturator (92) and cannula (94) (or needle (90)) without the user or another person or apparatus having to hold the combination of obturator (92) and cannula (94) (or needle (90)) at the desired orientation.

By way of example only, at least part of guide plate (300) near guide openings (306) may be formed of an elastomeric or otherwise flexible material, and one or more longitudinally extending wires (not shown) or other malleable members may be provided within such elastomeric or otherwise flexible material. Such wires may be made from a non-magnetic material such that no MRI artifact, or only a minimal MRI artifact, will occur during an associated imaging procedure. Some suitable materials for such wires may include, but are not limited to, cobalt alloys such as cobalt L605, aluminum alloys such as aluminum 6061, stainless steel alloys such as 316L stainless steel, titanium alloys such as titanium 6, nickel-cobalt alloys such as MP35N, and other suitable alloys. Alternatively, such wires may be formed of any other suitable materials or combinations of materials. A cannula (94), needle (90), or other instrument may be inserted into a selected guide opening (306) (e.g., before grid plate (300) is positioned adjacent to the patient's breast), and may then be angled to a desired position (e.g., providing a desired angular orientation for needle (90)). The action of such angling may cause such wires to undergo a plastic deformation such that the wires are malleable and hold their position once the cannula (94), needle (90), or other instrument reaches a desired orientation. The elastomeric nature of the portion of guide plate (300) at the selected guide opening (306) may allow guide opening (306) to conform to the angled orientation. Moreover, the construction of guide plate (300) may be such that the wires, once in their bent position, withstand any biasing forces by guide plate (300) that may attempt to return the guide opening (306) to its initial state; as well as any biasing forces that may be imposed by the weight of a coupled biopsy device (14). In such versions, the angled orientation of inserted biopsy device (14) may thus be maintained without the user or another person or apparatus holding biopsy device (14) at the desired position. Of course, in settings where an obturator (92) and cannula (94) are used, a user may first obtain a desired angular orientation with either cannula (94) or the combination of obturator (92) and cannula (94) before inserting needle (90) into cannula (94).

As one merely illustrative example of how another type of angulation feature may be provided, an adjustable bushing (not shown) may be positioned within a guide opening (306), and may include a rotating nut or other component that selectively provides locking and adjustability of the bushing. For instance, with the rotating nut or other component unlocking the bushing, the angular orientation of the bushing (and, hence, the angular orientation of the guide opening (306)) may be adjusted. The rotating nut or other component may then be manipulated to lock the adjusted angular orientation of the bushing (and, hence, the angular orientation of the guide opening (306)). Still other suitable ways in which an angulation feature may be provided will be apparent to those of ordinary skill in the art in view of the teachings herein.

While a several versions of grid plate (300) have been described above, other suitable features, configurations, components, functionalities, operability, and variations of grid plate (300) will be apparent to those of ordinary skill in the art in view of the teachings herein. It is therefore contemplated that grid plate (300) may take a variety of alternative forms and may be subject to a variety of alternative uses.

V. Alternative Guides

FIGS. 10-15B show examples of targeting guides (400, 450) that may be used in lieu of guide cube (104) described above. In particular, targeting guide (400, 450) may be inserted into a selected grid aperture (130) of guide plate (96) or a selected guide opening (306) of grid plate (300). Targeting guides (400, 450) may thus be used to guide insertion of one or more biopsy device (14) components into a patient's breast as described herein.

As shown in FIGS. 10-12 and 14-15B, targeting guide (400) of the present example comprises a substantially cylindraceous body (402) having a disc-shaped flange (404) at one end. A plurality of passageways (406, 408, 410) are formed through body (402) and flange (404). Flange (404) includes a knob (412), which may be used to rotate targeting guide (400) about the axis defined by body (402), such as to selectively position passageways (406, 408, 410) as will be described in greater detail below. Passageways (406, 408, 410) are each configured to insertingly receive cannula (94) or needle (90). For instance, in some versions, a combination of obturator (92) and cannula (90) are inserted into a patient's breast via a selected passageway (406, 408, 410) as described herein. Obturator (92) is then removed from cannula (94), and needle (90) is inserted into cannula (94) to obtain a tissue sample through side notch (218). Alternatively, cannula (94) and obturator (92) are not used in some other versions, such that needle (90) is inserted directly through a selected passageway (406, 408, 410) and into the patient's breast. In either case, targeting guide (400) may substantially support biopsy device (14) when needle (90) is disposed directly or indirectly in a selected passageway (406, 408, 410). Alternatively, some other component may directly support the weight of at least a portion of biopsy device (14).

It should be understood that a depth stop (95) may be used as described herein, to restrict the depth to which the combination of obturator (92) and cannula (94) (or needle (90), etc.) may be inserted through a selected passageway (406, 408, 410); and, hence, restrict the depth to which the combination of obturator (92) and cannula (94) (or needle (90), etc.) may be inserted into a patient's breast. Depth stop (95) may directly abut flange (404) of targeting guide (400). Alternatively, a depth stop (95) may be used in any other suitable fashion; or may be modified, substituted, supplemented, or even omitted, as desired.

In the present example, passageway (406) is positioned at the center of flange (404), such that passageway (406) is substantially coaxial with the longitudinal axis defined by body (402). Passageway (408) is positioned radially outwardly from passageway (406), such that the outer diameter of passageway (408) is tangent to the largest circle inscribed within grid aperture (130) when body (402) is inserted in grid plate (96) (FIG. 15A) as described in greater detail below. Passageway (410) is positioned at a diagonal of approximately 45° from passageway (406), such that the outer diameter of passageway (410) is tangent with the corner of grid aperture (130) when body (402) is inserted in grid plate (96) (FIG. 15A) as described in greater detail below. Of course, passageways (406, 408, 410) may alternatively be provided in any other suitable arrangement. In addition, in some other versions, passageways (406, 408, 410) are arranged such that at least one passageway (406, 408, 410) at least partially overlaps another passageway (406, 408, 410), such as like the overlapping guide holes shown in FIG. 18 of U.S. Pat. No. 7,507,210, entitled "Biopsy Cannula Adjustable Depth Stop," issued Mar. 24, 2009, the disclosure of which is incorporated by reference herein. Furthermore, while targeting guide (400) of the present example has three passageways (406, 408, 410), it should be understood that any other suitable number of passageways (406, 408, 410) may be provided in targeting guide (400), such more or less than three.

It should also be understood that passageways (406, 408, 410) may have any suitable size. For instance, as noted above, passageways (406, 408, 410) of the present example are sized to receive a cannula (94) or needle (90). In some settings, a user may have the option to use cannulas (94) and/or needles (90) of various gauges. Accordingly, some versions of targeting guide (400) may have passageways (406, 408, 410) of various sizes that accept cannulas (94) and/or needles (90) of various gauges. Alternatively, the size of passageways (406, 408, 410) in a given targeting guide (400) may be substantially consistent, with different targeting guides (400) being available that have passageways (406, 408, 410) of different sizes, such that the user may select a particular targeting guide (400) based on the gauge of the cannula (94) and/or needle (90) to be used. As yet another merely illustrative example, and as will be described in greater detail below, targeting guide (400) may be configured such that a given guide passageway (406, 408, 410) may accept cannulas (94) and/or needles (90) of different sizes. Still other suitable sizes for passageways (406, 408, 410) will be apparent to those of ordinary skill in the art in view of the teachings herein.

Figure 10:
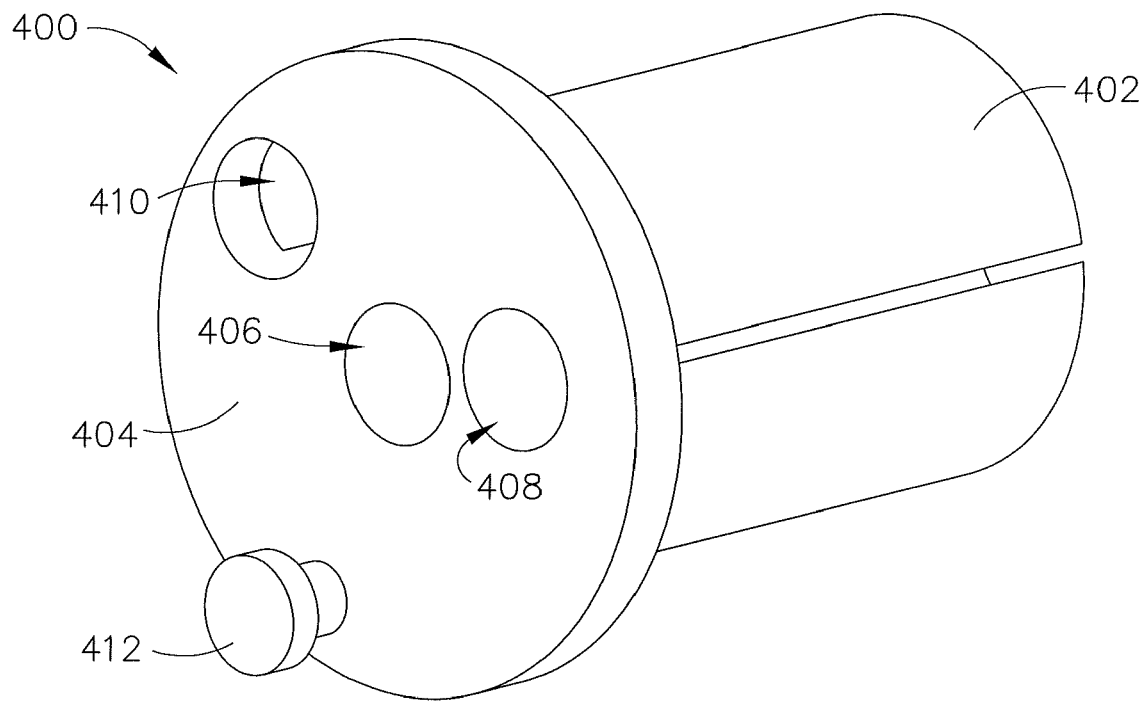
FIG. 10 is a front perspective view of an exemplary cylindraceous targeting guide.
Figure 11:
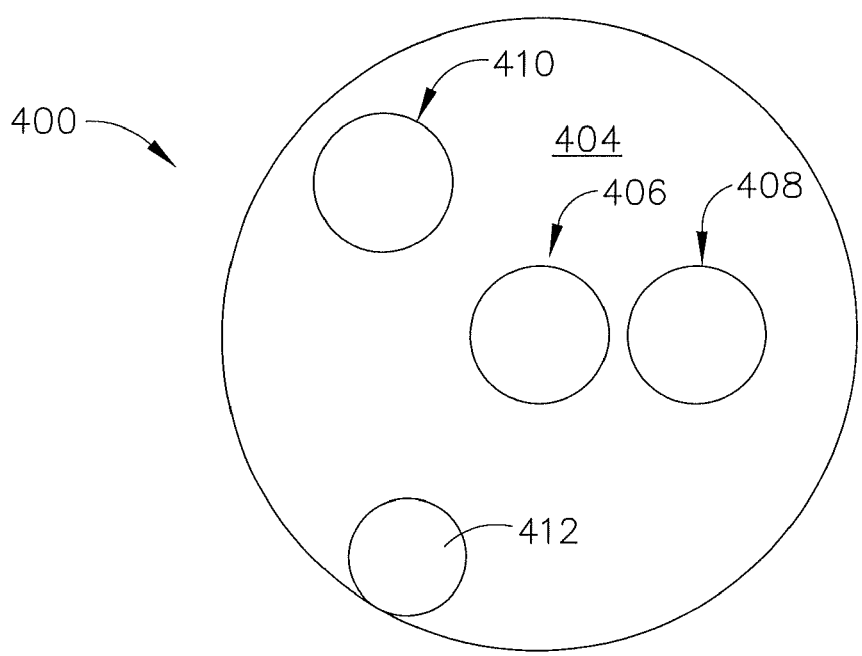
FIG. 11 is a front elevational view of the targeting guide of FIG. 10.
Figure 12:
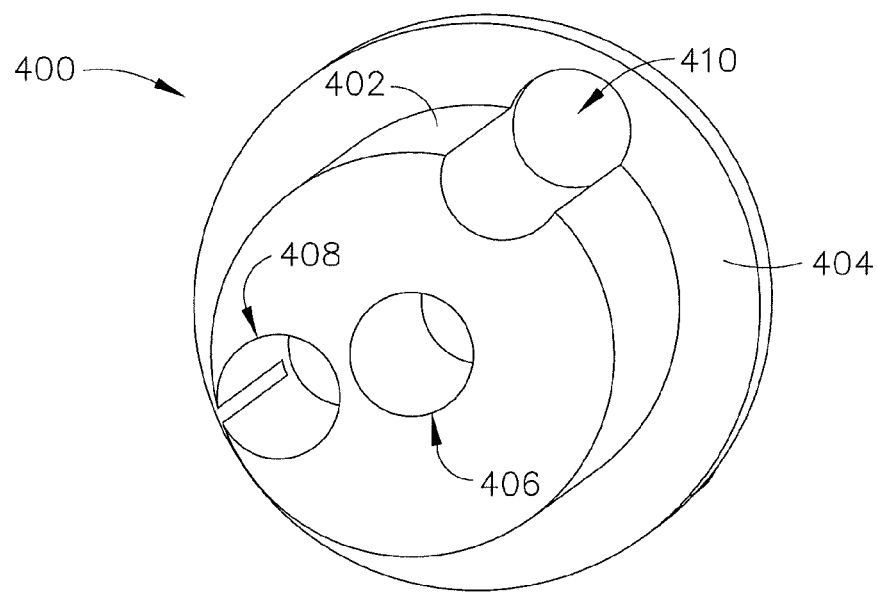
FIG. 12 is a rear perspective view of the targeting guide of FIG. 10.
Figure 15A:
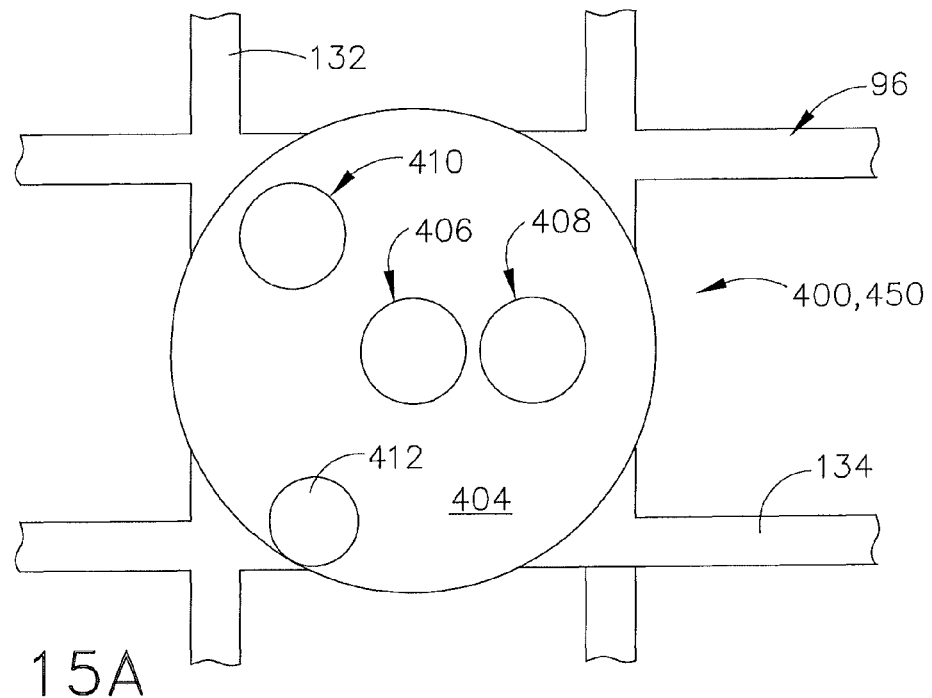
FIG. 15A is a front elevational view of the targeting guide and grid plate of FIG. 14, with the targeting guide at a first rotational position.

Passageways (406, 408, 410) of the present example are substantially round, and are configured to complement the cross-sectional shape of a cannula (94) or needle that will be inserted into passageways (406, 408, 410). By way of example only, passageways (406, 408, 410) may have a substantially circular cross-section, elliptical cross-section, oblong cross-section, "figure eight" type of cross-section, or any other suitable round cross-section. Alternatively, passageways (406, 408, 410) may have a non-round shape or may have any other suitable configuration. In addition, and as shown in FIGS. 10 and 12, passageways (408, 410) are positioned such that they pass through at least a portion of the longitudinal exterior surface of body (402). It should be understood that, in some such versions, a portion of a cannula (94) or needle (90) may directly engage at least a portion of grid plate (96) when the cannula (94) or needle (90) is disposed in such a passageway (408, 410). By way of example only, and with reference to the orientation of targeting guide (400) as shown in FIG. 15A, a portion of a cannula (94) or needle (90) that is disposed in passageway (410) may directly engage lip (140) and/or the upper left-hand corner of horizontal bar (132) and vertical bar (134). It should be understood, however, that passageways (406, 408, 410) in other versions of targeting guide (400) may not necessarily pass through at least a portion of the longitudinal exterior surface of body (402). A cannula (94) or needle (90) may thus be disposed in any selected passageway (406, 408, 410) of some versions of targeting guide (400) without such a cannula (94) or needle (90) necessarily contacting any portion of guide plate (96).

Targeting guide (400) of the present example is formed of a substantially rigid material, such as plastic. Of course, any other suitable material or combination of materials may be used. In addition, body (402) is dimensioned to fit snugly within grid aperture (130) of guide plate (96). In some other versions, targeting guide (400) is formed of an elastomeric material. Suitable elastomeric materials may include thermosetting plastics that may require vulcanization, thermoplastic elastomers (e.g., Santoprene™ among others), natural rubber, synthetic rubbers (e.g. ethylene propylene diene M-class—EPDM—among others), and/or any other suitable materials, including combinations of materials. For instance, with body (402) being formed of an elastomeric material, body (402) may conform with variations in dimensions of grid aperture (130). As another merely illustrative example, body (402) may be formed of a rigid plastic material with an elastomeric material overmolded about the exterior of body (402). Having an elastomeric material at the exterior of body (402) may facilitate fitting of body (402) in differently sized grid apertures (130) (e.g., in different types of grid plates (96), etc.); and may also reduce the likelihood of targeting guide (400) inadvertently falling out of grid plate (96).

Regardless of whether body (402) is formed in whole or in part of an elastomeric material, body (402) may have a tapered configuration in some versions. For instance, body (402) may be configured such that its outer diameter is greater at the rear face of flange (404) than the outer diameter at the free end of body (402). Such a tapered configuration may permit body (402) of targeting guide (400) to securely interface with the grid aperture (130) in the grid plate (96) by inserting body (402) in the grid plate (96) up to the point where the tapered body (402) contacts the interior walls of the grid aperture (130) in the grid plate (96). In some settings, such an interface may be securely provided regardless of whether the interior walls of the grid aperture (130) in the grid plate (96) are substantially horizontal and vertical along their length or at non-horizontal and/or non-vertical angles along their length. It should also be understood that such a tapered configuration of body (402) may permit a given targeting guide (400) to be used with different grid plates (96) having grid apertures (130) of different sizes (e.g., selectively use targeting guide (400) with a grid plate (96) having grid apertures (130) of one size or use the same targeting guide (400) with a grid plate (96) having grid apertures (130) of a different size, etc.). Unless otherwise explicitly stated herein, the term "cylindraceous" shall be read to include bodies (402) having a purely cylindrical shape as well as bodies (402) having a tapered shape (e.g., frusto-conical, etc.).

In addition to or in lieu of providing an elastomeric material at the exterior of body (402), an elastomeric material may be provided within the interior of passageways (406, 408, 410), such as by forming interior regions of body (402) out of elastomeric material, by providing elastomeric inserts within passageways (406, 408, 410), or otherwise. Providing elastomeric properties or similar properties in passageways (406, 408, 410) may reduce the likelihood that in instrument (e.g., needle (90) of biopsy device (14), a combination of cannula (94) and obturator (92), etc.) that is inserted through a selected passageway (406, 408, 410) will inadvertently slip along its longitudinal axis, inadvertently rotate about its longitudinal axis, etc. Providing elastomeric properties or similar properties in passageways (406, 408, 410) may also permit passageways (406, 408, 410) to snugly accept insertion of cannulas (94) and/or needles (90) of different gauges. It should therefore be understood that the entirety of body (402) may be formed of an elastomeric material, that at least a portion of the exterior of body (402) may be formed of an elastomeric material, or that at least a portion of the interior of passageways (406, 408, 410) may be formed of an elastomeric material. It should also be understood that when at least a portion of the interior of passageways (406, 408, 410) is formed of an elastomeric material, passageways (406, 408, 410) may be formed as longitudinally extending slits through such elastomeric material (e.g., instead of being formed as lumens having circular or otherwise round cross-sections along their length, etc.).

In addition to or in lieu of providing an elastomeric material within passageways (406, 408, 410), a malleable material or other angulation feature may be provided in or by passageways (406, 408, 410). For instance, in some settings, it may be desirable to insert a combination of obturator (92) and cannula (94) (or needle (90)) into a patient's breast at a non-orthogonal angle (e.g., non-perpendicular to the plane defined by flange (404)). Having malleable material or some other type of angulation feature may permit a user to adjust the angular orientation of a selected passageway (406, 408, 410) to provide such a non-orthogonal axis of penetration. In some such versions, the malleable material or angulation feature may permit the axis of penetration angle to be adjusted yet still maintain the adjusted axis of penetration angle after insertion of the combination of obturator (92) and cannula (94) (or needle (90)) without the user or another person or apparatus having to hold the combination of obturator (92) and cannula (94) (or needle (90)) at the desired orientation.

By way of example only, at least part of body (402) near passageways (406, 408, 410) may be formed of an elastomeric or otherwise flexible material, and one or more longitudinally extending wires (not shown) or other malleable members may be provided within such elastomeric or otherwise flexible material. Such wires may be made from a non-magnetic material such that no MRI artifact, or only a minimal MRI artifact, will occur during an associated imaging procedure. Some suitable materials for such wires may include, but are not limited to, cobalt alloys such as cobalt L605, aluminum alloys such as aluminum 6061, stainless steel alloys such as 316L stainless steel, titanium alloys such as titanium 6, nickel-cobalt alloys such as MP35N, and other suitable alloys. Alternatively, such wires may be formed of any other suitable materials or combinations of materials. A cannula (94), needle (90), or other instrument may be inserted into a selected passageway (406, 408, 410) (e.g., before grid plate (96) is positioned adjacent to the patient's breast), and may then be angled to a desired position (e.g., providing a desired angular orientation for needle (90)). The action of such angling may cause such wires to undergo a plastic deformation such that the wires are malleable and hold their position once the cannula (94), needle (90), or other instrument reaches a desired orientation. The elastomeric nature of the portion of body (402) at the selected passageway (406, 408, 410) may allow body (402) to conform to the angled orientation. Moreover, the construction of targeting guide (400) may be such that the wires, once in their bent position, withstand any biasing forces by body (402) that may attempt to return the selected passageway (406, 408, 410) to its initial state; as well as any biasing forces that may be imposed by the weight of a coupled biopsy device (14). In such versions, the angled orientation of inserted biopsy device (14) may thus be maintained without the user or another person or apparatus holding biopsy device (14) at the desired position. Of course, in settings where an obturator (92) and cannula (94) are used, a user may first obtain a desired angular orientation with either cannula (94) or the combination of obturator (92) and cannula (94) before inserting needle (90) into cannula (94).

As one merely illustrative example of how another type of angulation feature may be provided, an adjustable bushing (not shown) may be positioned within a passageway (406, 408, 410), and may include a rotating nut or other component that selectively provides locking and adjustability of the bushing. For instance, with the rotating nut or other component unlocking the bushing, the angular orientation of the bushing (and, hence, the angular orientation of the passageways (406, 408, 410)) may be adjusted. The rotating nut or other component may then be manipulated to lock the adjusted angular orientation of the bushing (and, hence, the angular orientation of the passageways (406, 408, 410)). Still other suitable ways in which an angulation feature may be provided will be apparent to those of ordinary skill in the art in view of the teachings herein.

Figure 13:
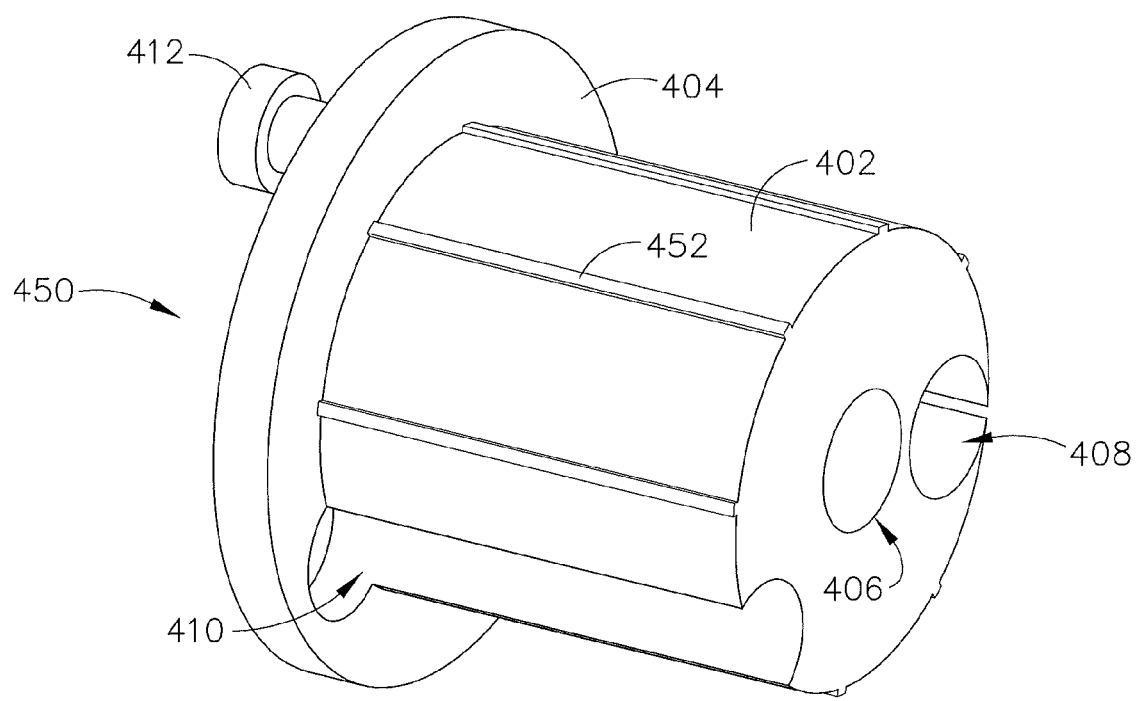
FIG. 13 is a side perspective view of an exemplary alternative cylindraceous targeting guide.

FIG. 13 shows a merely illustrative variation of targeting guide (400). In particular, FIG. 13 shows targeting guide (450), which includes the same features of and has the same operability of targeting guide (400) as described herein, but which also includes longitudinally extending ribs (452). Ribs (452) extend the full length of body (402) in this example, and are spaced equidistantly about the exterior of body (402). Alternatively, ribs (452) may extend to any other suitable length; and may be at any other suitable spacing relative to each other. Ribs (452) may facilitate longitudinal retention of targeting guide (450) within grid plate (96) and/or reduce the risk of inadvertent rotation of targeting guide (450) about the longitudinal axis defined by targeting guide (450) when targeting guide (400) is inserted in grid plate (96). Ribs (452) may be rigid, elastomeric, or have any other suitable properties. It should also be understood that a variety of other features may be provided on the exterior of body (402) in addition to or in lieu of ribs (452), including but not limited to flats (e.g., ten to twenty or more flats), circumferentially extending ribs, discrete bumps, other types of protrusions, knurling, etc. Unless otherwise explicitly stated herein, the term "cylindraceous" shall be read to include bodies (402) having a purely cylindrical shape as well as bodies (402) having ribs (452) or other similar features.

Figure 14:
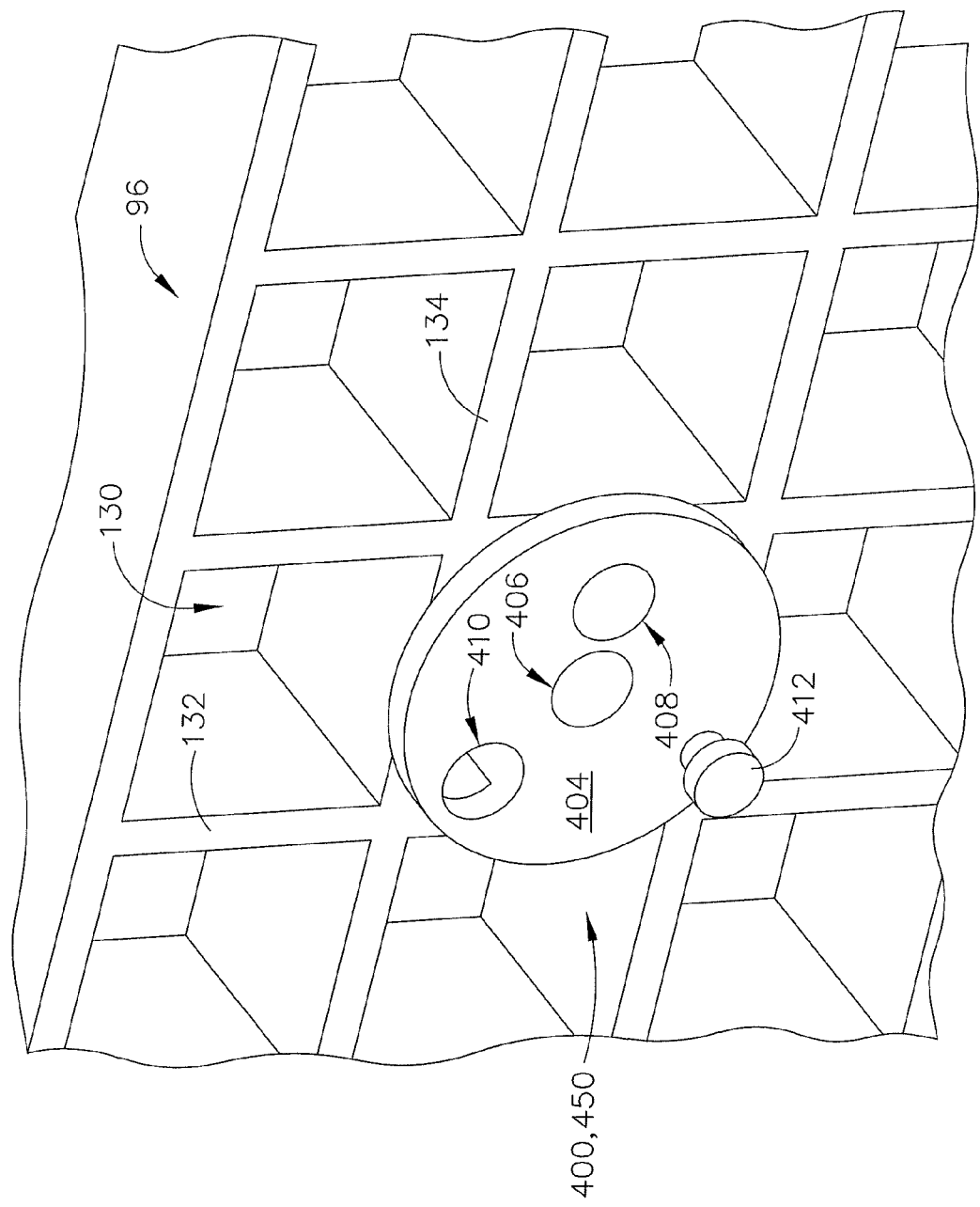
FIG. 14 is a perspective view of the targeting guide of FIG. 10 inserted in the grid plate of FIG. 6.

As noted above, either type of targeting guide (400, 450) may be inserted into a selected grid aperture (106) of grid plate (96). As shown in FIG. 14, targeting guide (400, 450) may be inserted into a selected grid aperture (130) until flange (404) abuts bars (132, 134) of grid plate (96). Alternatively, as also noted above, either type of targeting guide (400, 450) may be inserted into a selected guide opening (306) of some versions of grid plate (300) (e.g., in versions of grid plate (300) where guide openings (306) are too large to accept just a cannula (94) or needle (90) but are large enough to accept a targeting guide (400, 450)). Similar to the engagement between targeting guide (400, 450) and grid plate (96), the engagement between targeting guide (400, 450) and grid plate (300) may be such that flange (404) abuts first face (302) of grid plate (300). Of course, targeting guide (400, 450) may alternatively be coupled with a variety of other types of grid plates having various configurations; or may be coupled with any other suitable structures.

Figure 15B:
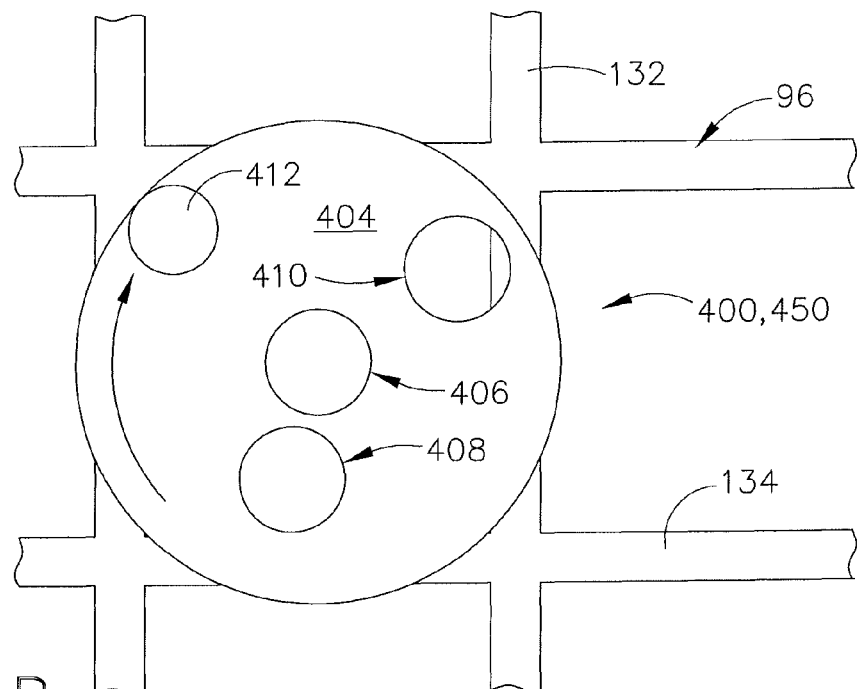
FIG. 15B is a front elevational view of the targeting guide and grid plate of FIG. 14, with the targeting guide rotated to a second rotational position.

As shown in FIGS. 15A-15B, targeting guide (400, 450) may be rotated within grid aperture (130) when body (402) is inserted in grid plate (96). In particular, FIG. 15A shows targeting guide (400, 450) in a first rotational position; while FIG. 15B shows targeting guide (400, 450) in a second rotational position. A user may rotate targeting guide (400, 450) by grasping knob (412) and using it to rotate targeting guide (400, 450) about the longitudinal axis defined by targeting guide (400, 450). Such rotatability of targeting guide (400, 450) may present the user with a virtually infinite number of rotational positions and corresponding patterns of passageways (406, 408, 410), providing a significant degree of access to breast tissue. It should also be understood that some versions of targeting guide (400, 450) may permit such rotatability while targeting guide (400, 450) is inserted in grid plate (96); while other versions of targeting guide (400, 450) may require withdrawal from and re-insertion into grid plate (96) to effect rotational adjustments. While FIGS. 15A-15B depict targeting guide (400, 450) as being rotatable within grid aperture (130) when targeting guide (400, 450) is inserted into grid plate (96), it should also be understood that targeting guide (400, 450) may be rotatable within guide opening (306) when targeting guide (400, 450) is inserted into grid plate (300).

While a several versions of targeting guide (400, 450) have been described above, other suitable features, configurations, components, functionalities, operability, and variations of targeting guide (400, 450) will be apparent to those of ordinary skill in the art in view of the teachings herein. It is therefore contemplated that targeting guide (400, 450) may take a variety of alternative forms and may be subject to a variety of alternative uses.

Versions of the present invention may have application in conventional endoscopic and open surgical instrumentation as well as application in robotic-assisted surgery.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A guide device for guiding a biopsy instrument relative to a patient, the biopsy instrument comprising an elongate portion having a cross-section, the guide device comprising:
   (a) a first face;
   (b) a second face opposing the first face;
   (c) a plurality of passageways extending from the first face to the second face, wherein the passageways each have a cross-section complementing the cross-section of the elongate portion of the biopsy instrument; and
   (d) one or more malleable members disposed on or about a wall defining a perimeter within at least one passageway, wherein the one or more malleable members do not substantially restrict access to the at least one passageway, and wherein the one or more malleable members do not project beyond the first face or the second face;
   wherein the guide device is configured to cooperate with a compression member to compressively secure a portion of a patient between the guide device and the compression member;
   wherein a selected one of the passageways is configured to guide the elongate portion of the biopsy instrument into the secured portion of the patient as the elongate portion of the biopsy instrument is inserted into the selected one of the passageways.

2. The guide device of claim 1, wherein the guide device comprises a plate.

3. The guide device of claim 1, wherein the passageways each have a substantially round cross-section.

4. The guide device of claim 3, wherein the passageways each have a substantially circular cross-section.

5. The guide device of claim 1, wherein the first face defines a first plane, wherein the second face defines a second plane, wherein the passageways each define a respective longitudinal axis, wherein the first plane and the second plane are substantially parallel, wherein the longitudinal axes are substantially perpendicular to the first and second planes.

6. The guide device of claim 1, wherein the passageways are spaced substantially equidistantly relative to each other.

7. The guide device of claim 1, wherein the guide device comprises a substantially rigid material.

8. The guide device of claim 7, wherein at least one passageway is defined by the substantially rigid material.

9. The guide device of claim 7, wherein the guide device further comprises an elastomeric material.

10. The guide device of claim 9, wherein the passageways are defined by the elastomeric material.

11. The guide device of claim 10, wherein the one or more malleable members are associated with the elastomeric material defining each passageway, wherein the elastomeric material defining each passageway is configured to permit adjustment of the angle defined by each passageway relative to the first face.

12. The guide device of claim 11, wherein the one or more malleable members comprises one or more deformable wires, wherein the one or more deformable wires are configured to substantially maintain an adjusted angle defined by an adjusted passageway relative to the first face.

13. The guide device of claim 1, wherein the biopsy instrument has a weight, wherein the guide device is configured to support the weight of the biopsy instrument when the elongate portion of the biopsy instrument is inserted into a selected one of the passageways.

14. A biopsy guide system, comprising:
   (a) a biopsy instrument, wherein the biopsy instrument comprises:
      (i) an elongate cannula having a round cross-section, and
      (ii) a tissue penetrating tip disposed at a distal end of the elongate cannula; and
   (b) a guide plate, wherein the guide plate comprises:
      (i) a first face,
      (ii) a second face, and
      (iii) a plurality of passageways defined by an elastomeric material, the plurality of passageways extending from the first face to the second face, wherein each passageway of the plurality of passageways has a round cross-section, and
      (iv) one or more deformable members associated with the elastomeric material defining each passageway, wherein the elastomeric material defining each passageway is configured to permit adjustment of the angle defined by each passageway relative to the first face;
   wherein the guide plate is configured to cooperate with a compression member to compressively secure a portion of a patient between the guide device and the compression member;
   wherein the elongate cannula is inserted through a passageway selected from the plurality of passageways.

15. The biopsy guide system of claim 14, wherein the passageways are defined by interior surfaces of the guide plate, wherein the cannula directly contacts the interior surface of the guide plate defining the selected passageway.

16. The biopsy guide system of claim 14, further comprising a depth stop positioned on the elongate cannula, wherein the depth stop contacts the first face of the guide plate to restrict the distance to which the elongate cannula is inserted in the selected passageway.

17. The biopsy guide system of claim 14, wherein the guide plate further comprises an elastomeric material, wherein the elastomeric material contacts the elongate cannula at the selected passageway.

18. The biopsy guide system of claim 14, wherein the elongate cannula comprises a needle of a biopsy probe.

19. A guide device for guiding a biopsy instrument relative to a patient, the biopsy instrument comprising an elongate portion having a cross-section, the guide device comprising:
   (a) a first face;
   (b) a second face opposing the first face; and
   (c) a plurality of passageways extending from the first face to the second face, wherein the passageways each have a round cross-section, wherein the passageways are sized to insertingly receive a biopsy instrument guide having a cylindraceous body;
   wherein the guide device is configured to cooperate with a compression member to compressively secure a portion of a patient between the guide device and the compression member; and
   (d) a biopsy instrument guide, wherein the biopsy instrument guide is inserted in a selected one of the passageways, wherein the biopsy instrument guide comprises a cylindraceous body and a knob, wherein the biopsy instrument guide is rotatable via the knob within the selected passageway about an axis defined by the cylindraceous body, wherein the biopsy instrument guide has at least one guide passageway extending through the cylindraceous body, wherein the knob does not define the at least one guide passageway, wherein the at least one guide passageway of the biopsy instrument guide has a cross-section complementing the cross-section of the elongate portion of the biopsy instrument.

20. The guide device of claim 19, wherein the biopsy instrument guide has at least one off-center guide passageway such at the at least one off-center guide passageway is rotatable from a first rotational position to a second rotational position, wherein the first rotational position is different from the second rotational position.

* * * * *